(12) United States Patent
Beaudoin et al.

(10) Patent No.: US 6,800,299 B1
(45) Date of Patent: Oct. 5, 2004

(54) METHOD OF EXTRACTING LIPIDS FROM MARINE AND AQUATIC ANIMAL TISSUES

(75) Inventors: Adrien Beaudoin, Rock Forest (CA); Geneviéve Martin, Sherbrooke (CA)

(73) Assignee: Universite de Sherbrooke (CA)

( * ) Notice: Subject to any disclaimer, the term of this patent is extended or adjusted under 35 U.S.C. 154(b) by 0 days.

(21) Appl. No.: 09/830,146

(22) PCT Filed: Oct. 21, 1999

(86) PCT No.: PCT/CA99/00987

§ 371 (c)(1),
(2), (4) Date: Jul. 25, 2001

(87) PCT Pub. No.: WO00/23546

PCT Pub. Date: Apr. 27, 2000

(30) Foreign Application Priority Data

Oct. 21, 1998 (CA) ............................................. 2251265

(51) Int. Cl.[7] .............................................. A61K 35/56
(52) U.S. Cl. ...................................... 424/522; 424/523
(58) Field of Search ................................ 424/522, 523, 424/94.1, 94.2

(56) References Cited

U.S. PATENT DOCUMENTS

| | | | |
|---|---|---|---|
| 4,331,695 A | | 5/1982 | Zosel |
| 5,006,281 A | | 4/1991 | Rubin et al. |
| 6,055,936 A | * | 5/2000 | Collin .......................... 11/215 |

FOREIGN PATENT DOCUMENTS

| | | | |
|---|---|---|---|
| CA | 1098900 | | 4/1981 |
| CA | 2115571 | | 5/1993 |
| EP | 0732378 | | 9/1996 |
| JP | 53112195 | | 9/1978 |
| JP | 60 035057 | | 2/1985 |
| JP | 360035057 | * | 2/1985 |
| JP | 04 057853 | | 2/1992 |
| JP | 04057853 | | 2/1992 |
| JP | 08198754 | | 6/1996 |
| JP | 08198754 | | 8/1996 |
| NO | 147365 | | 5/1982 |
| WO | WO 8401715 | | 5/1984 |

OTHER PUBLICATIONS

Patent Abstracts of Japan, Jul. 2, 1976, JP 51 076467.
Patent Abstracts of Japan vo. 009, No. 059, Mar. 15, 1985, JP 59196032.
Thomas Carell, Edward A. Wintner, A. Bashir–Hashemi, Julius Rebek, Jr. "A Novel Procedure for the Synthesis of Libraries Containing Small Organic Molecules". Angew. Chem. Int. Ed. Engl. 1994, 33, No. 20; p. 2059.
Thomas Carell, Edward A. Wintner, Julius Rebek, Jr. "A Solution–Phase Screening Procedure for the Isolation of Active Compounds from a Library of Molecules". Angew. Chem. Int. Ed. Engl. 1994, 33, No. 20; p. 2061.

Marie–Thèrése Château, Céline Ginestier–Verne, Jean Chiesa, René Caravano, Jean Paul Bureau. "Dimethyl sul-foxide–induced apoptosis in human leukemic U937 cells". *Analytical Cellular Pathology* 10 (1996) 75–84.

Takashi Kojima, Masao Yamamoto, Chihiro Mochizuki, Toshihio Mitake, Norimasa Sawada and Yohichi Mochizuki. "Different Changes in Express and Function of Connexin 26 and Connexin 32 During DNA Synthesis and Redifferentitation in Primary Rat Hepatocytes Using a DMSO Culture System" *Hepatology*, Sep. 1997; vol. 26, No. 3, 1997.

Kit S. Lam. "Application of conbinatorial library methods in cancer research and drug discovery". *Anti–Cancer Drug Design* (1997), 12, 145–167.

Jose Prados, Consolacion Melguizo, Juan Emilio Fernandez, Amelia Eva Aranega, Luis Alvarea and Antonia Arangea. "Actin, Tropomyosin and α–Actinin as Markers of Differ-entiation in Human Rhabdomyosarcoma Cell Lines Induced with Dimethyl Sulfoxide". *Cellular Molecular Biology*. 39(5) 525–536, 1993.

Howard M. Prentice, Stephen E. Moore, John G. Dickson, Patrick Doherty and Frank S. Walsh. "Nerve growth fac-tor–induced changes in neural cell adhesion molecule (N–CAM) in PC12 cells". *The EMBO Journal*, vol. 6, No. 7, pp. 1859–1863, 1987.

Stefan Sjolander and Csaba Urbaniczky, "Integrated Fluid Handling System for Biomolecular Interaction Analysis". *Analytical Chemistry*, vol. 63, No. 29, Oct. 15, 1991.

Alexander Szabo, Lesley Stolz and Russ Granzow.. "Surface plasmon resonance and its use in biomolecular interaction analysis (BIA)".

O. Trubiani, C. Peiri, M. Rapino, R. DiPrimo. "The c–myc gene regulats the polyamine pathway in DMSO–induced apoptosis". *Cell Proliferation*, 1999, 32, 119–129.

R.A. Houghten, J.R. Appel, S.E. Blondelle, J.H. Curevo, C.T. Dooler and C. Pinilla. "The Use of Synthetic Peptide Combinatorial Libraries for the Identification of Bioactive Peptides" *BioTechniques* vol. 13, No. 3 (1992).

\* cited by examiner

*Primary Examiner*—Jean C. Witz
(74) *Attorney, Agent, or Firm*—Akerman Senterfitt

(57) ABSTRACT

Provided herein is a method for extracting lipid fractions from marine and aquatic animal material by acetone extrac-tion. The resulting non-soluble and particulate fraction is preferably subjected to an additional solvent extraction with an alcohol, preferably ethanol, isopropanol or t-butanol or an ester of acetic acid, preferably ethyl acetate to achieve extraction of the remaining soluble lipid fraction from the marine and aquatic animal material. The remaining non-soluble particulate contents is also recovered since it is enriched in proteins and contains a useful amount of active enzymes. Also provided herein is a krill extract.

39 Claims, 20 Drawing Sheets

FIG_1

| | | |
|---|---|---|
| 1.263 | 4.521 — 16:1 | 11.637 |
| 1.455 — 12:0 | 4.684 | 12.145 — 18:3 |
| 1.625 | 4.891 — 16:1tr | 13.458 |
| 1.812 | 5.121 | 15.626 — 20:0 |
| 1.876 | 5.426 | 16.045 |
| 2.056 | 5.570 | 16.482 — 20:1 |
| 2.173 | 6.037 | 17.017 — 20:1(cis11) |
| 2.331 — 14:0 | 6.662 | 19.344 — 20:2 |
| 2.505 | 6.871 | 22.606 — 20:4(6,10,14,18) |
| 2.591 — 14:1 | 7.235 | 24.103 |
| 2.682 | 7.925 — 18:0 | 26.247 |
| 2.802 | 8.439 — 18:1 | 28.287 |
| 2.855 | 8.640 — 18:1tr | 31.295 |
| 3.078 — std 15:0 | 9.544 | 40.655 |
| 3.309 | 9.801 — 18:2 | 49.721 |
| 3.586 | 10.491 | 56.373 |
| 3.810 | 10.825 | 62.225 |
| 4.176 — 16:0 | 11.042 | |

| | | |
|---|---|---|
| 1.217 | 3.806 | 9.786 − 18:2 |
| 1.264 | 4.157 − 16:0 | 10.484 |
| 1.454 − 12:0 | 4.515 − 16:1 | 10.813 |
| 1.624 | 4.680 | 11.590 |
| 1.812 | 4.891 − 16:1tr | 12.136 − 18:3 |
| 1.876 | 5.028 | 13.447 |
| 2.055 | 5.109 | 15.623 − 20:0 |
| 2.171 | 5.421 | 16.025 |
| 2.330 − 14:0 | 5.562 | 16.466 − 20:1 |
| 2.505 | 6.031 | 17.021 − 20:1 (cis11) |
| 2.591 − 14:1 | 6.642 | 22.585 − 20:4 (6,10,14,18) |
| 2.680 | 6.870 | 24.100 |
| 2.800 | 7.230 | 26.217 |
| 2.854 | 7.910 − 18:0 | 28.241 |
| 3.077 − std 15:0 | 8.419 − 18:1 | 40.622 |
| 3.306 | 8.622 − 18:1tr | 56.417 |
| 3.585 | 9.529 | 62.086 |

FIG_3

| | | |
|---|---|---|
| 1.216 | 4.520 − 16:1 | 13.457 |
| 1.262 | 4.683 | 13.943 |
| 1.454 − 12:0 | 4.884 − 16:1tr | 15.053 |
| 1.624 | 5.030 | 15.572 − 20:0 |
| 1.811 | 5.111 | 16.016 |
| 1.875 | 5.420 | 16.486 − 20:1 |
| 2.016 | 5.561 | 16.999 − 20:1(cis11) |
| 2.054 | 6.031 | 18.762 |
| 2.174 | 6.642 | 19.303 − 20:2 |
| 2.330 − 14:0 | 6.868 | 20.474 |
| 2.505 | 7.226 | 21.027 − 20:3 |
| 2.589 − 14:1 | 7.908 − 18:0 | 22.575 − 20:4 (6,10,14,18) |
| 2.679 | 8.444 − 18:1 | 24.071 |
| 2.799 | 8.639 − 18:1tr | 26.215 |
| 2.854 | 9.005 | 28.333 |
| 2.981 | 9.536 | 31.180 |
| 3.074 − std 15:0 | 9.788 − 18:2 | 40.560 |
| 3.304 | 10.267 | 46.595 |
| 3.580 | 10.481 | 49.513 |
| 3.804 | 10.807 | 56.292 |
| 4.169 − 16:0 | 11.626 | 62.250 |
| 4.296 | 12.140 − 18:3 | |

| | | |
|---|---|---|
| 1.552 – 12:0 | 5.675 – 16:1tr | 12.888 |
| 1.749 | 5.964 | 13.388 |
| 1.968 | 6.284 | 14.017 |
| 2.095 | 6.533 | 14.524 – 18:3 |
| 2.262 | 6.655 | 16.107 |
| 2.485 | 7.009 | 19.275 – 20:0 |
| 2.582 – 14:0 | 7.159 | 20.112 – 20:1 (cis11) |
| 2.784 | 7.440 | 20.781 – 20:1 |
| 2.886 – 14:1 | 7.874 | 27.553 |
| 3.004 | 8.019 | 29.529 |
| 3.145 | 8.462 | 32.161 |
| 3.478 – std 15:0 | 9.411 – 18:0 | 34.614 |
| 3.720 | 10.000 – 18:1 | 39.240 |
| 4.088 | 10.249 – 18:1tr | 50.374 |
| 4.325 | 10.716 | 61.892 |
| 4.793 – 16:0 | 11.357 | 70.568 |
| 5.196 – 16:1 | 11.647 – 18:2 | 77.894 |
| 5.406 | 12.519 | |

FIG_5

| | | |
|---|---|---|
| 1.556 – 12:0 | 5.977 | 14.540 – 18:3 |
| 1.753 | 6.294 | 16.133 |
| 1.972 | 6.546 | 16.805 |
| 2.104 | 7.020 | 18.131 |
| 2.304 | 7.166 | 19.154 – 20:0 |
| 2.590 – 14:0 | 7.889 | 19.875 |
| 2.892 – 14:1 | 8.030 | 20.099 – 20:1(cis11) |
| 3.012 | 8.473 | 20.820 – 20:1 |
| 3.153 | 9.425 – 18:0 | 23.903 |
| 3.485 – std 15:0 | 10.010 – 18:1 | 27.583 |
| 3.710 | 10.260 – 18:1tr | 29.570 |
| 4.096 | 10.735 | 32.195 |
| 4.203 | 11.394 | 34.597 |
| 4.333 | 11.661 – 18:2 | 39.334 |
| 4.800 – 16:0 | 12.540 | 50.452 |
| 5.206 – 16:1 | 12.909 | 70.660 |
| 5.417 | 13.402 | 77.895 – 24:0 |
| 5.711 – 16:1tr | 14.010 | |

FIG_6

| | | |
|---|---|---|
| 1.564 – 12:0 | 8.025 | 34.677 |
| 1.762 | 8.485 | 38.373 – 22:0 |
| 1.977 | 9.360 – 18:0 | 40.163 |
| 2.080 | 9.407 | 50.157 |
| 2.273 | 10.147 – 18:1tr | 57.532 |
| 2.591 – 14:0 | 11.618 – 18:2 | 61.436 |
| 2.887 – 14:1 | 12.858 | 70.271 |
| 3.008 | 14.515 – 18:3 | 77.784 – 24:0 |
| 3.470 – std 15:0 | 16.162 | 110.694 |
| 4.108 | 18.077 | 127.696 |
| 4.341 | 19.355 – 20:1 | |
| 4.803 – 16:0 | 20.182 – 20:4 (cis11) | |
| 5.210 – 16:1tr | 20.311 | |
| 5.683 | 23.205 – 20:2 | |
| 6.292 | 24.678 | |
| 6.514 | 27.411 – 20:4 (6,10,14,18) | |
| 7.030 | 29.307 | |
| 7.810 | 31.990 | |

Cholesterol esters
Methyl esters

Triglycerides

Free fatty acids
Cholesterol
Diglycerides
Monoglycerides
Origin

Neutral lipids

Cephalin

Lecithin
Sphingomyelin
Lysolecithin
Origin

METHOD OF EXTRACTING LIPIDS FROM MARINE AND AQUATIC ANIMAL TISSUES

FIELD OF THE INVENTION

This invention relates to the extraction of lipid fractions from marine and aquatic animals such as krill, Calanus, fish and sea mammals. More specifically, this invention relates to an improved method of extracting lipid fractions by dehydration with solvents and recovering a solid residue rich in active enzymes.

BACKGROUND OF THE INVENTION

Lipid fractions obtained from marine and aquatic animals such as krill, Calanus, fish and sea mammals have various applications:

Medical Applications

Marine and aquatic animal oils and fractions thereof contain various therapeutic agents. For example, it is reported that various marine and aquatic animal oils have anti-inflammatory properties. Marine and aquatic animal oils are also reported as helpful in reducing the incidence of cardiovascular disease. Also, some marine and aquatic animal oils are reported as suppressing the development of certain forms of lupus and renal diseases. As a further example, krill may be used as a source of enzymes for debridement of ulcers and wounds or to facilitate food digestion. Also marine and aquatic oils contain various antioxidants, which may have potential therapeutic properties.

Nutraceuticals

Considering the beneficial effects of omega-3 fatty acids, oils from krill, Calanus and fish could be used as dietary supplements to human diet. These fatty acids are essential for proper development of the brain and the eye. Marine and aquatic animal oils are also rich in liposoluble vitamins A, D and E and carotenoids.

Cosmetics

Various marine and aquatic animal oils are used for the production of moisturizing creams.

Fish Farming

Among the lipids found in krill, Calanus and fish, high concentrations of fatty acids 20:5 (eicosapentaenoic acid) and 22:6 (docosahexaenoic acid) are present. These fatty acids are essential nutrients and are beneficial as fish feed. Furthermore, these essential nutrients are carried over in human diet by eating the fish grown on such diets.

Animal Feed

Animal feed diets rich in omega-3 fatty acids may increase the level of unsaturated fatty acids and decrease cholesterol levels of meat. This property is already exploited in the poultry industry to improve the quality of eggs.

Various methods for extracting marine and aquatic animal oils are known. For example, it is known to extract fish oil using organic solvents such as hexane and ethanol. It is also known to measure the fat content in fish muscle tissue using solvents such as acetone.

U.S. Pat. No. 4,331,695 describes a method using pressurized solvents which are gaseous at room temperature, such as propane, butane or hexane. The extraction is performed at preferred temperatures of 15 to 80° C. on shredded vegetable or finely divided animal products. The extracted oils are then made to precipitate under high pressure and elevated temperatures of 50 to 200° C. However, hexane is a poor extraction solvent for marine animals such as krill. Furthermore, the high temperatures used in the precipitation step negatively alters the lipids.

Canadian Patent Application 2,115,571 describes a method for extracting oils from various brown and read algae species. The method provides for example Soxhlet extraction using nearly pure ethanol for 40 hours.

U.S. Pat. No. 5,006,281 describes a method for extracting oil from marine and aquatic animals such as fish. The marine and aquatic animal is first treated with an antioxidant compound, finely divided and centrifuged to separate the oil phase from the aqueous phase and solid phase. The oil phase is then further treated with antioxidant to remove undesirable odour or taste.

Canadian Patent 1,098,900 describes a method for extracting oils from krill. The method involves emulsifying fresh or defrosted krill in an aqueous medium. The oil fraction is recovered by centrifugation.

Folch in the article published in the year 1957 in J. biol. Chem. 226: 497–509 "A simple method for the isolation and purification of total lipids from animal tissues" proposes an extraction method using chloroform and methanol. This method is not commercially feasible because of the toxicity of the solvents involved.

However, prior art processes are generally commercially unfeasible or provide low quantitative yields. Thus, it is an object of the present invention to provide an improved marine and aquatic animal oil extraction method allowing recovery of a valuable lipid fraction and separate recovery of a valuable protein rich solid residue that comprises active enzymes.

Other objects and further scope of applicability of the present invention will become apparent from the detailed description given hereinafter. It should be understood, however, that this detailed description, while indicating preferred embodiments of the invention, is given by way of illustration only, since various changes and modifications within the spirit and scope of the invention will become apparent to those skilled in the art.

DETAILED DESCRIPTION OF THE PREFERRED EMBODIMENT

Figure 1:
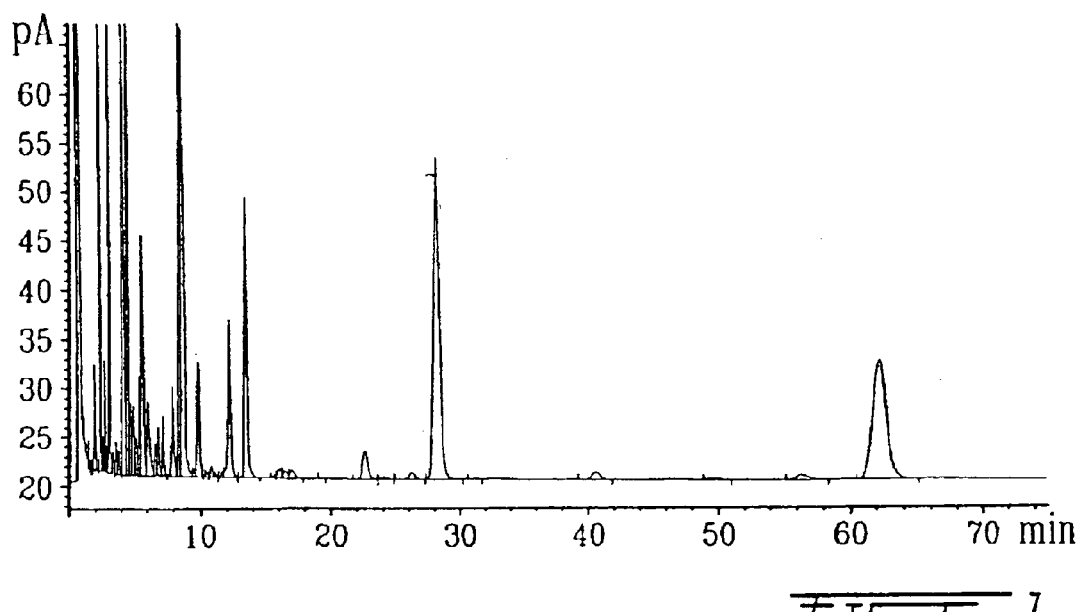
FIG. 1. Gas-liquid chromatography of fatty acids from dry krill (chloroform-methanol)
Figure 2:
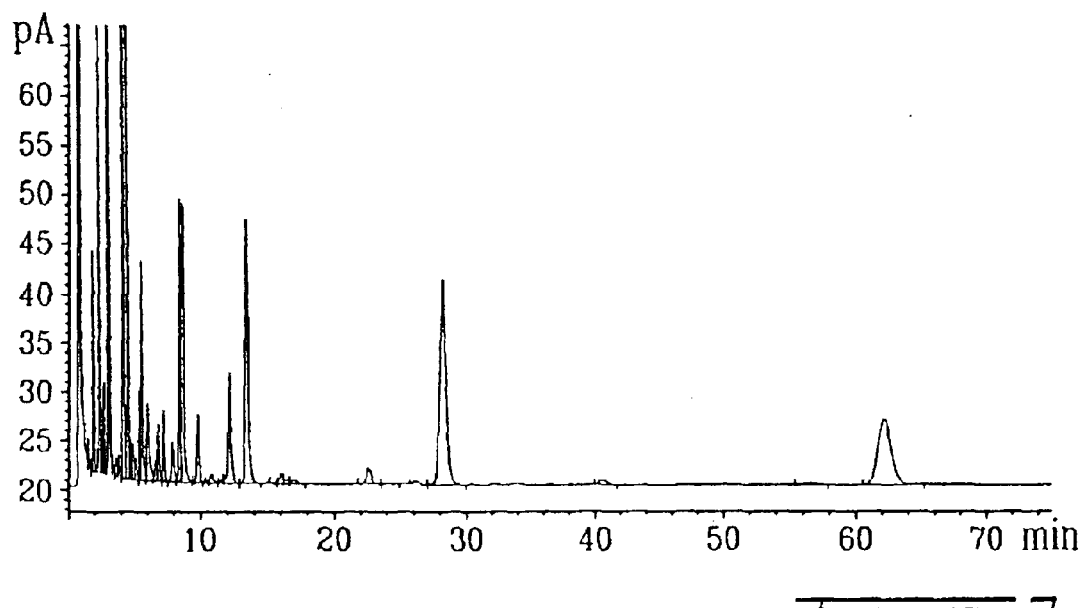
FIG. 2. Gas-liquid chromatography of fatty acids from dry krill (acetone)
Figure 3:
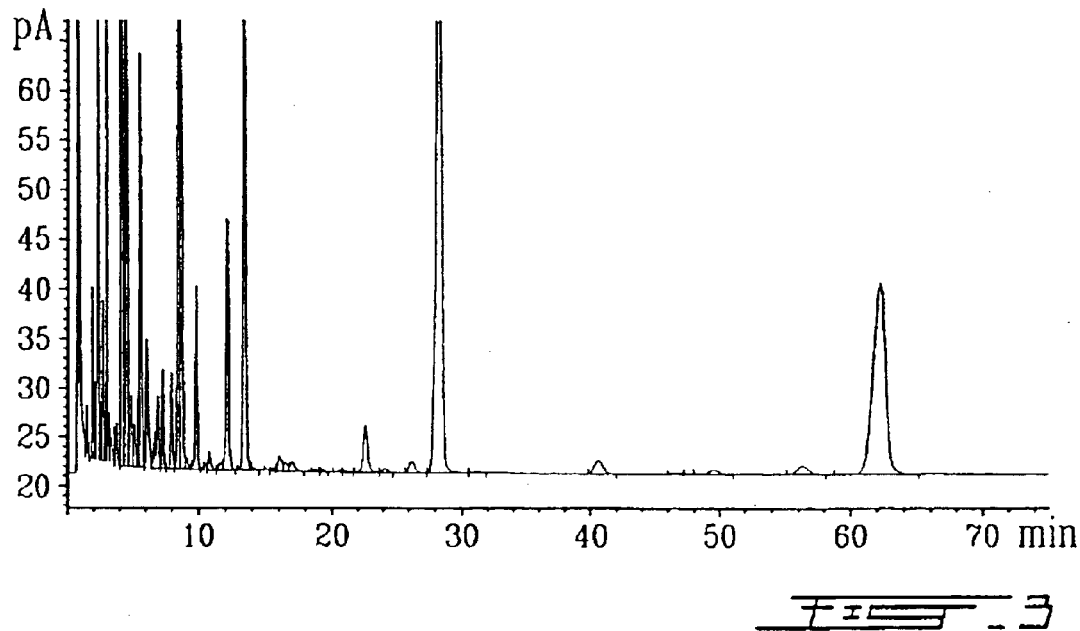
FIG. 3. Gas-liquid chromatography of fatty acids from frozen krill (acetone)
Figure 4:
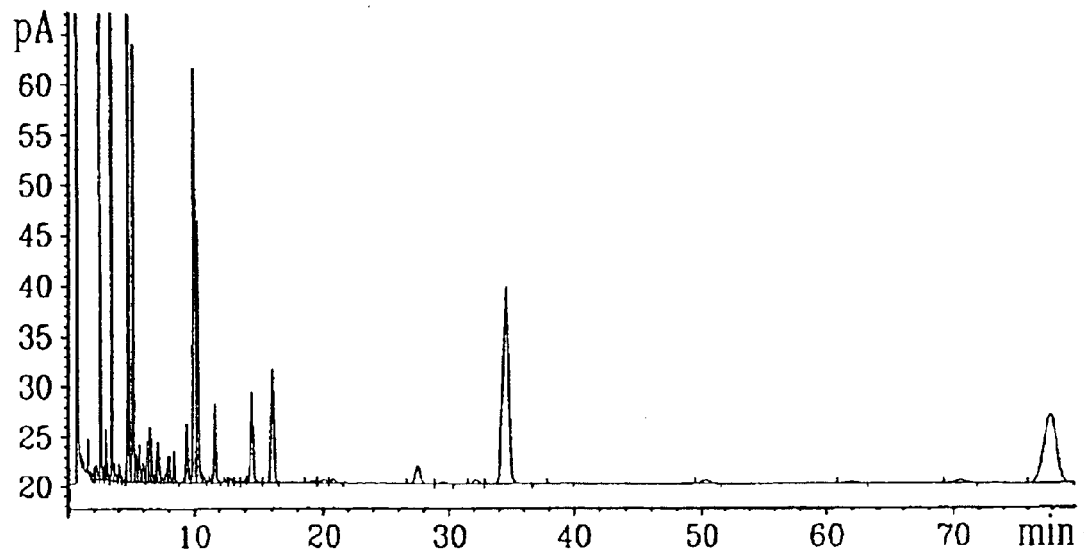
FIG. 4. Gas-liquid chromatography of fatty acids from frozen krill (ethanol)
Figure 5:
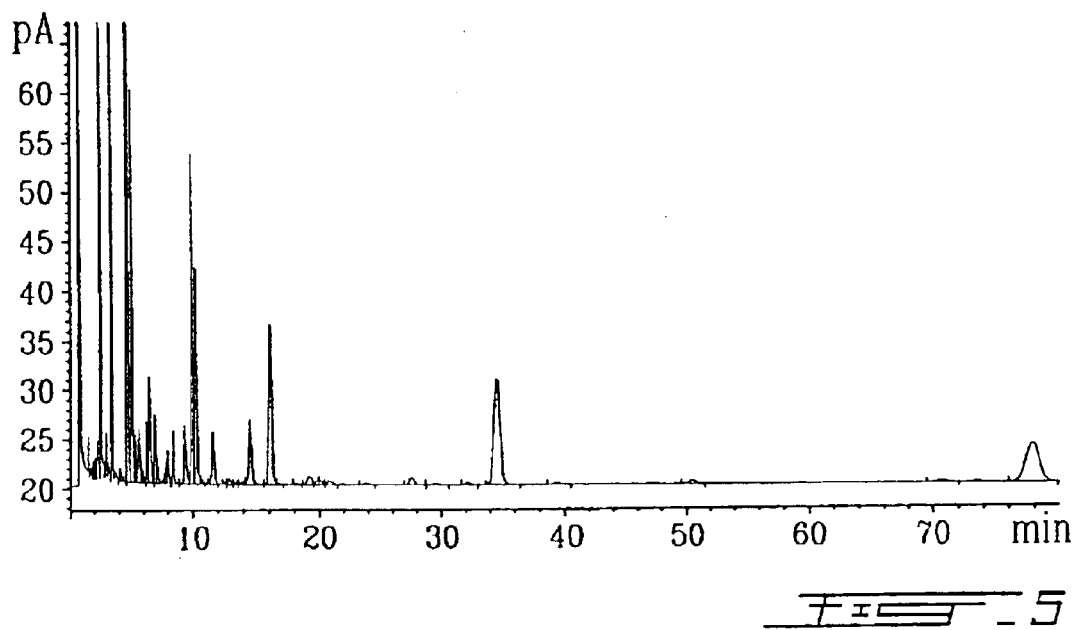
FIG. 5. Gas-liquid chromatography of fatty acids from frozen krill (t-butanol)
Figure 6:
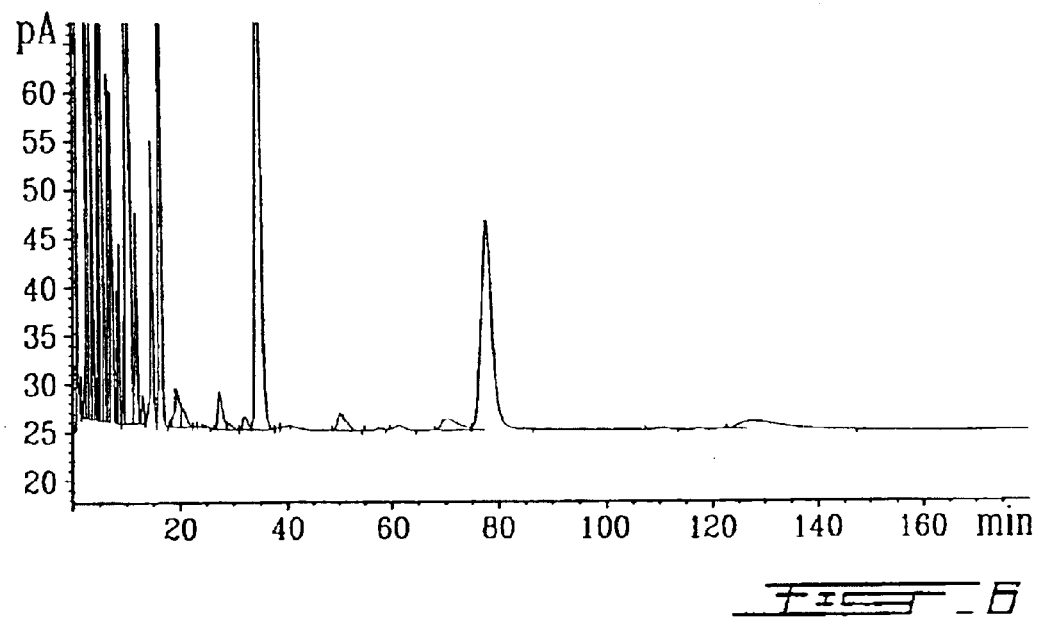
FIG. 6. Gas-liquid chromatography of fatty acids from frozen krill (ethyl acetate)
Figure 7:
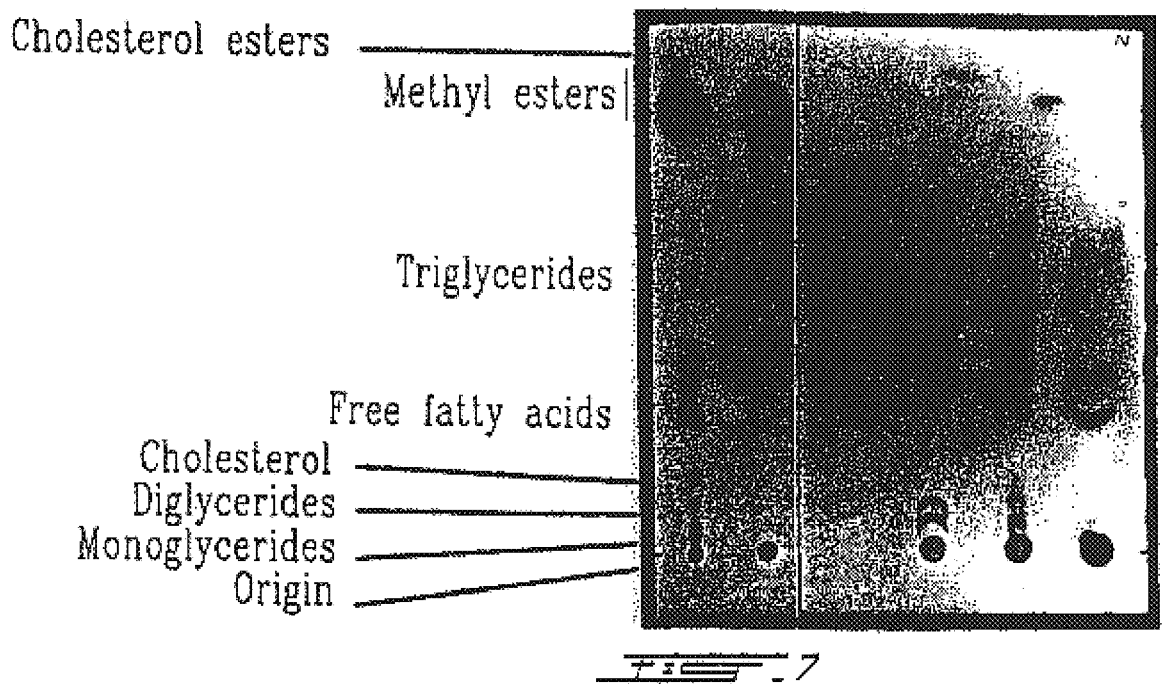
FIG. 7. Thin-layer chromatography of neutral lipids of Calanus sp. and *M. norvegica*
Figure 8:
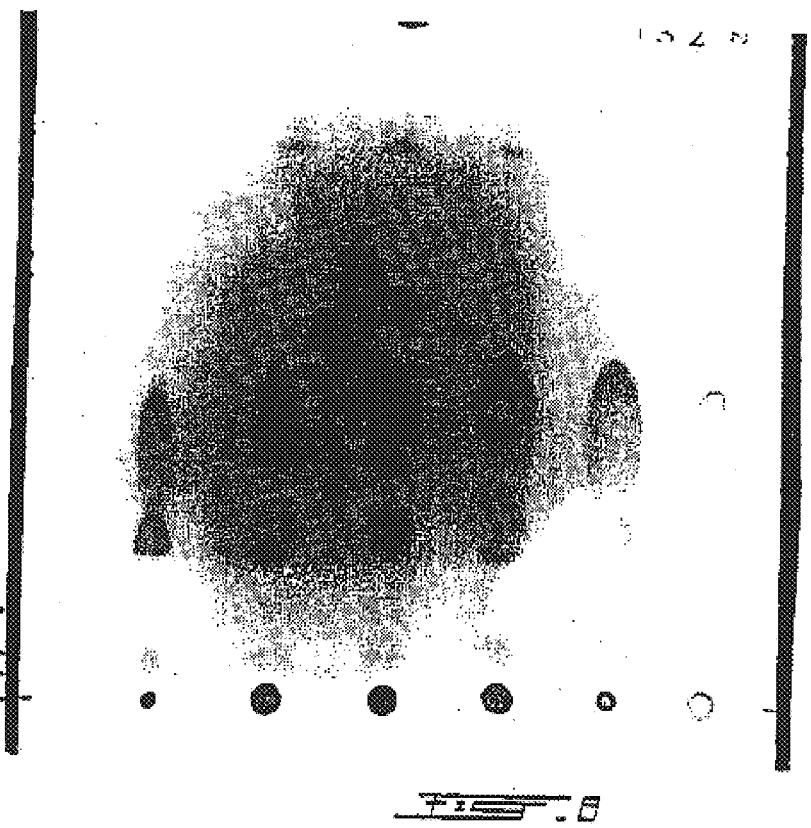
FIG. 8. Thin-layer chromatography of neutral lipids of *E. pacifica*
Figure 9:
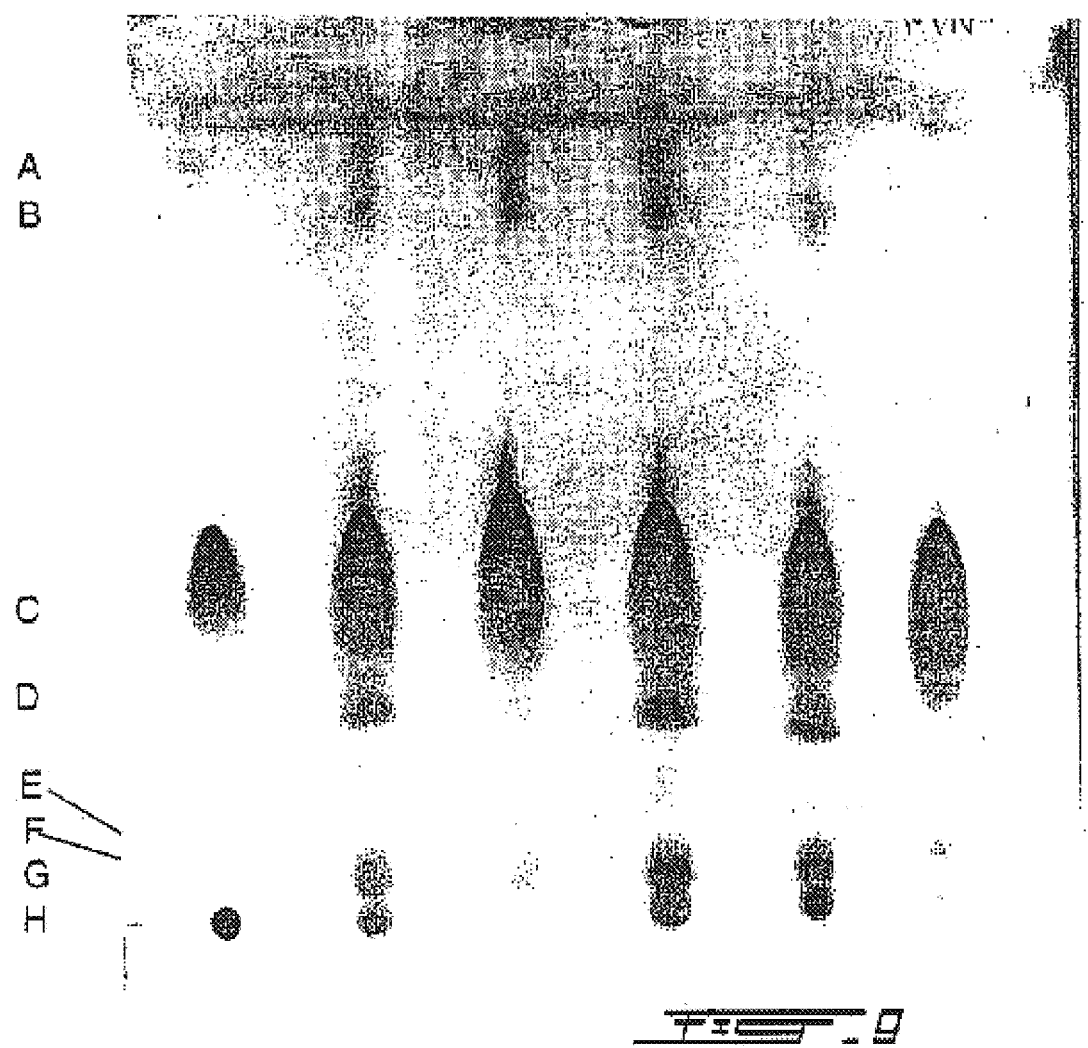
FIG. 9. Thin-layer chromatography of neutral lipids of *M. schmitti*
Figure 10:
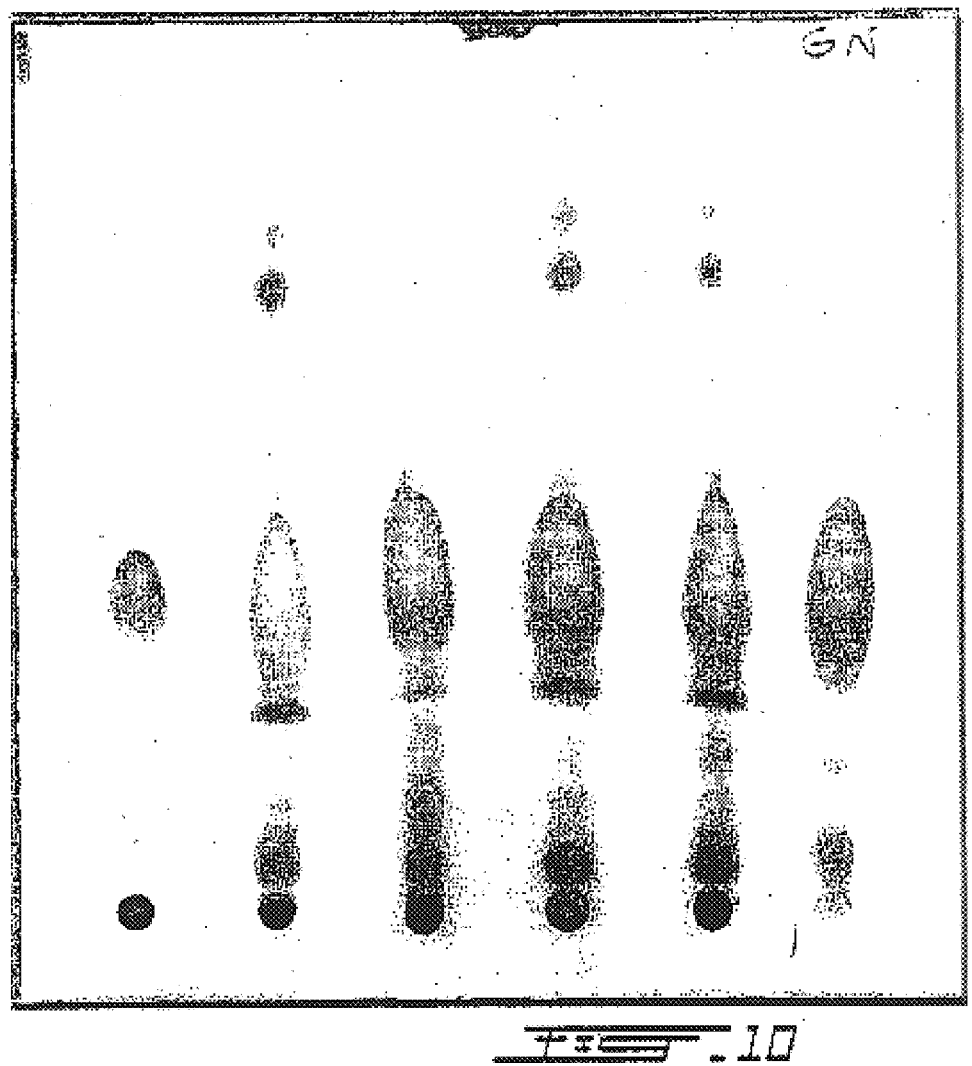
FIG. 10. Thin-layer chromatography of neutral lipids of *G. galeus*
Figure 11:
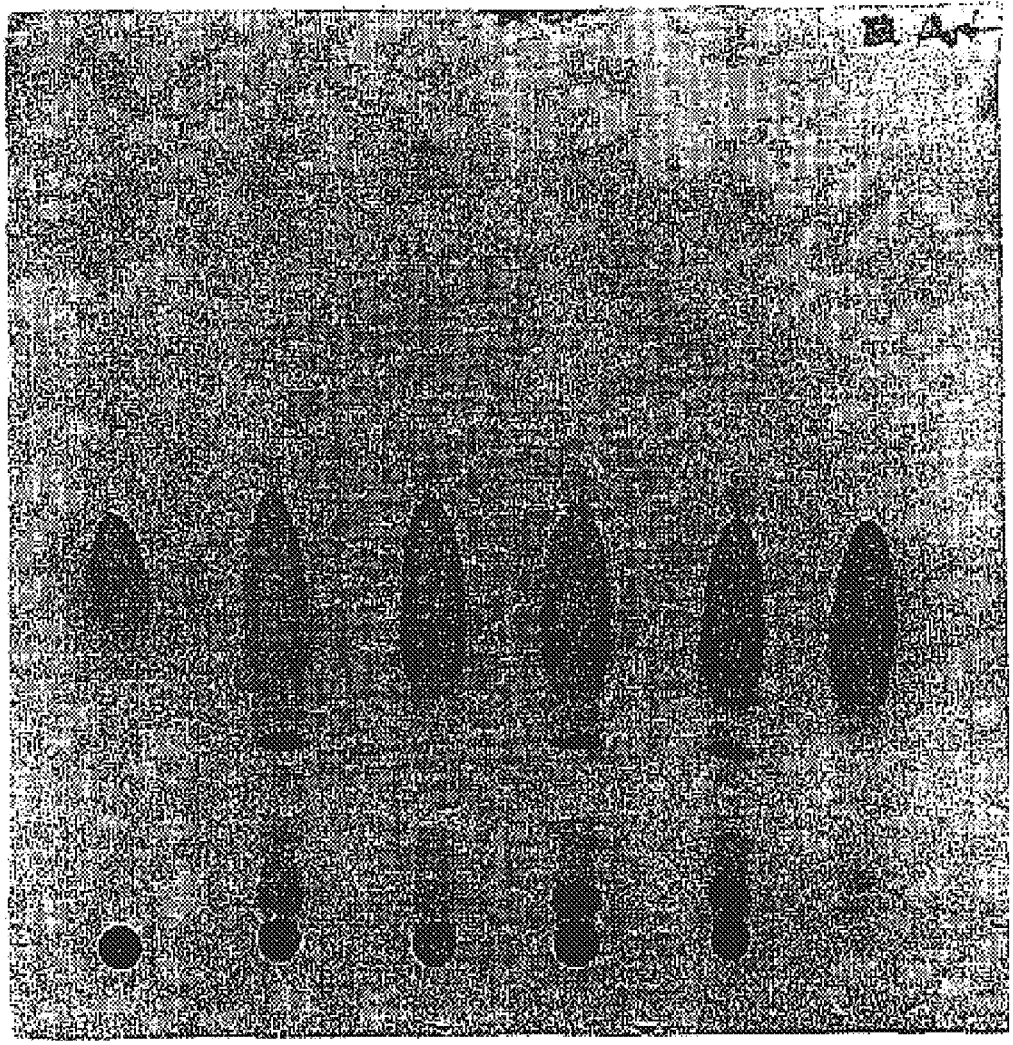
FIG. 11. Thin-layer chromatography of neutral lipids of Angel Shark
Figure 12:
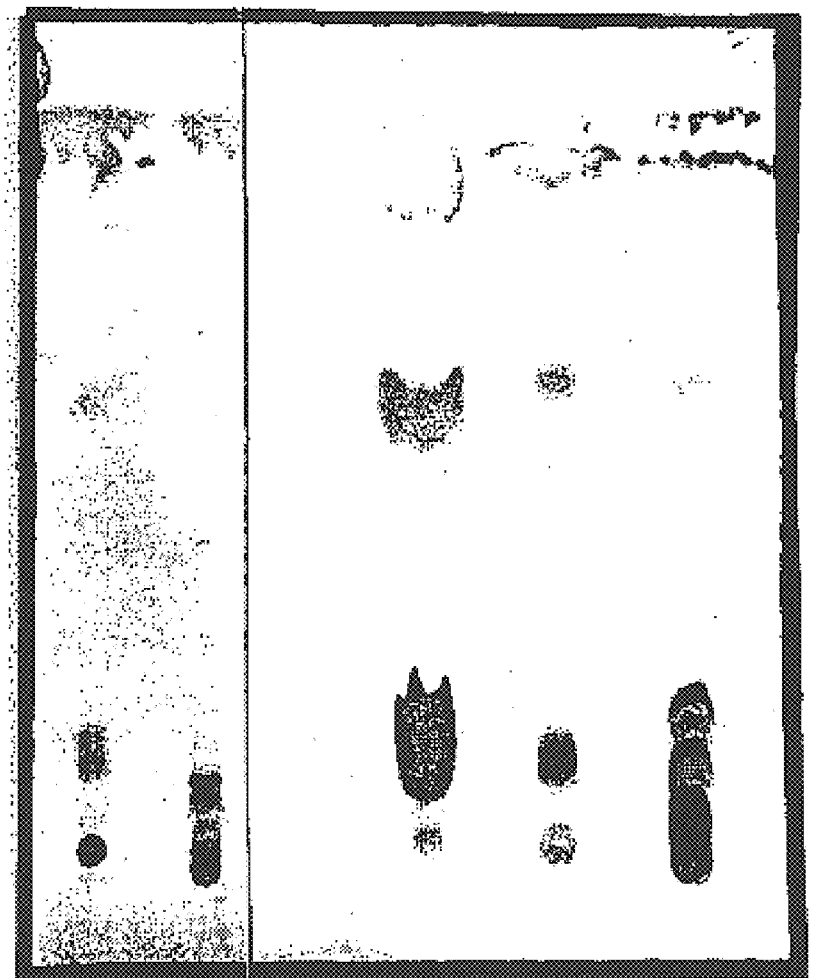
FIG. 12. Thin-layer chromatography of phospholipids of Calanus sp. and *M. norvegica*
Figure 13:
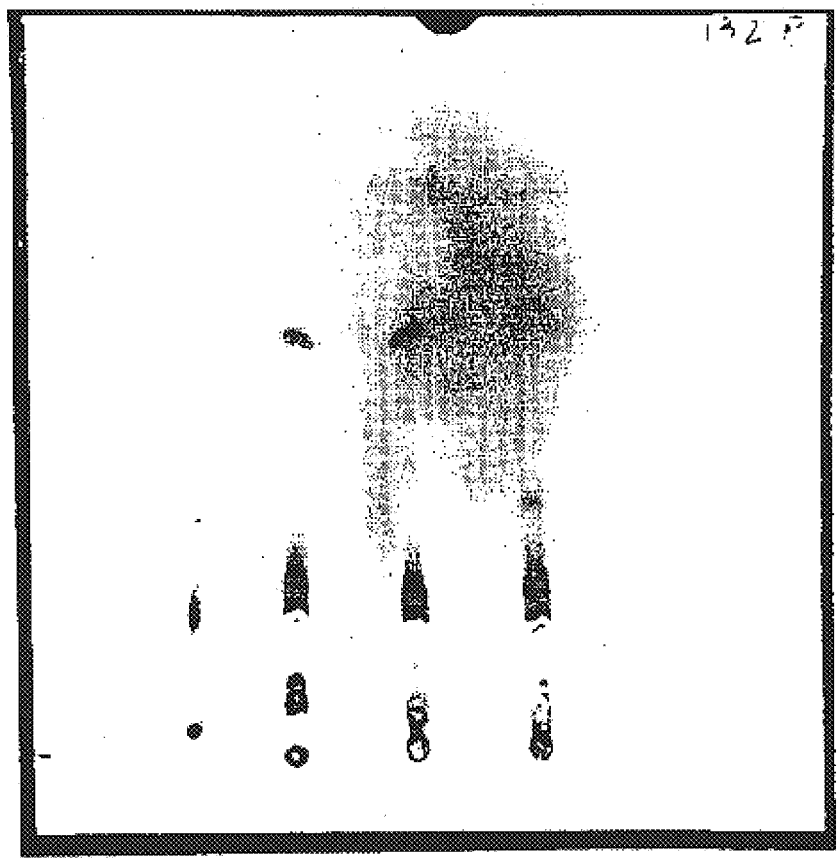
FIG. 13. Thin-layer chromatography of phospholipids of *E. pacifica*
Figure 14:
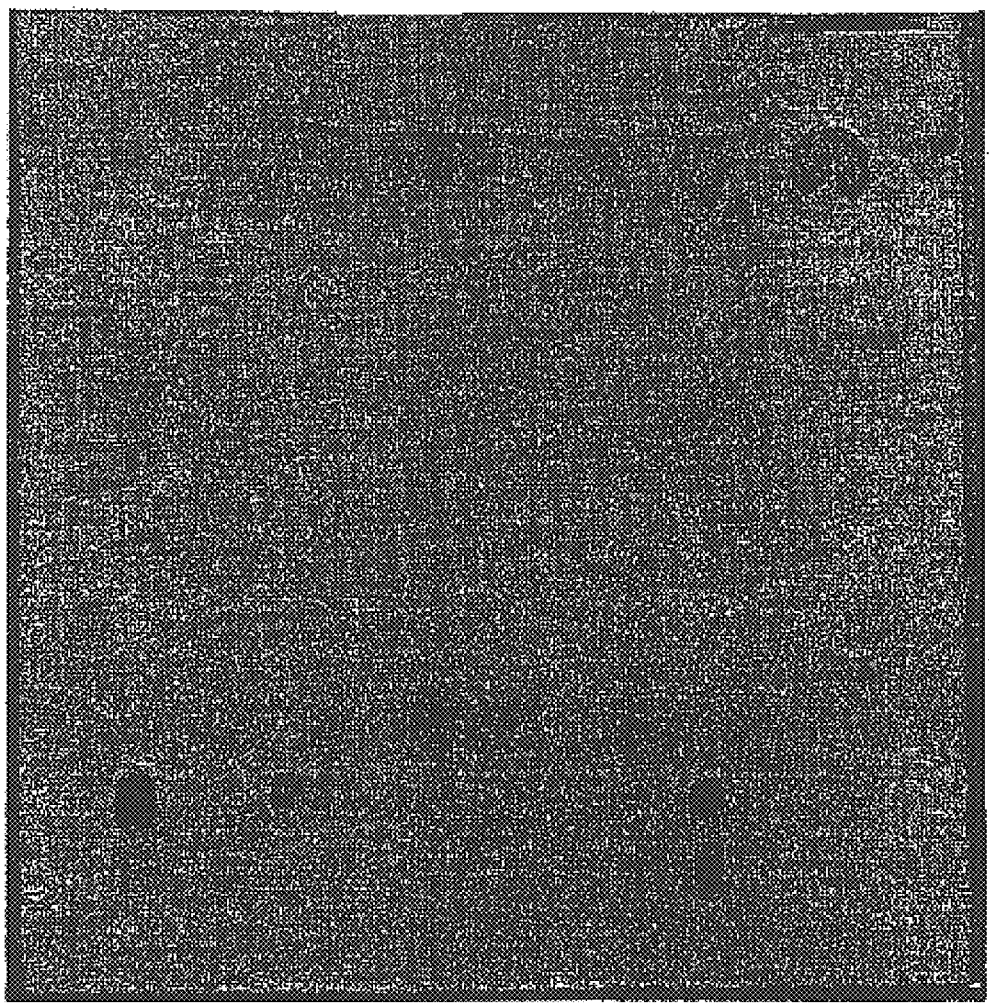
FIG. 14. Thin-layer chromatography of phospholipids of *M. schmitti*
Figure 15:
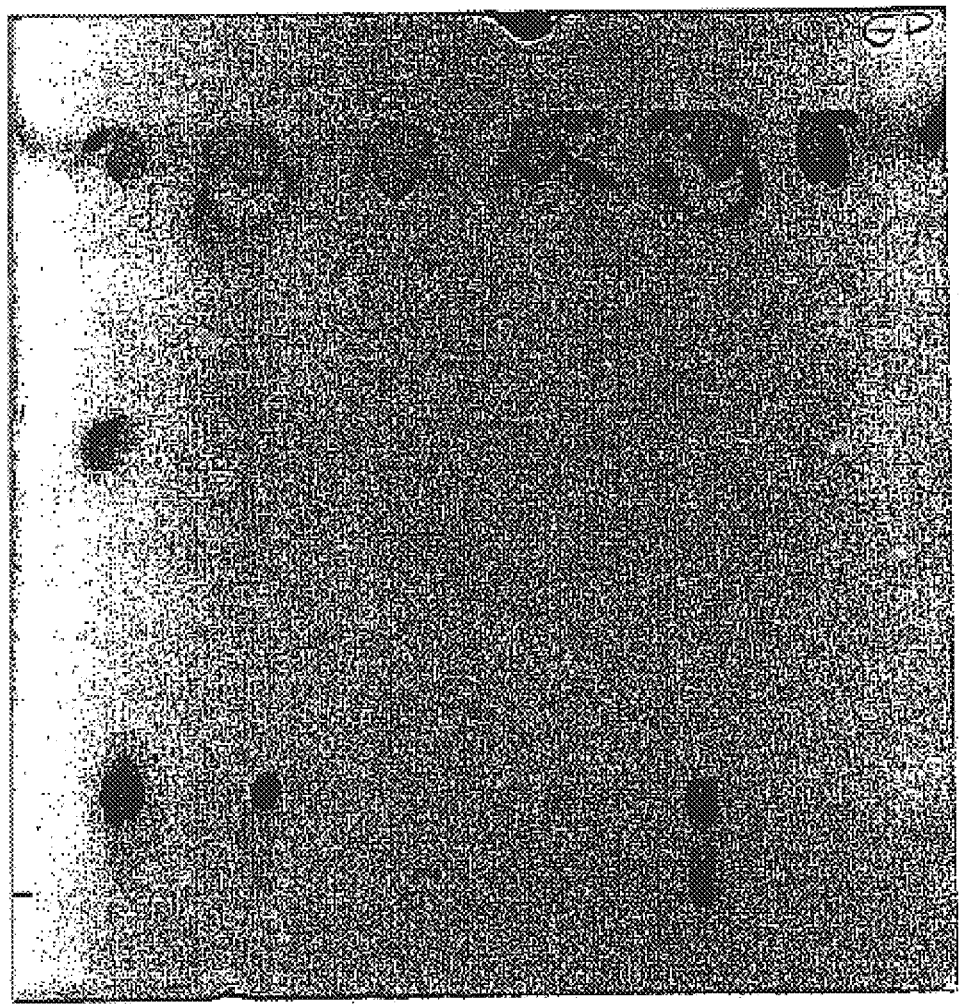
FIG. 15. Thin-layer chromatography of phospholipids of *G. galeus*
Figure 16:
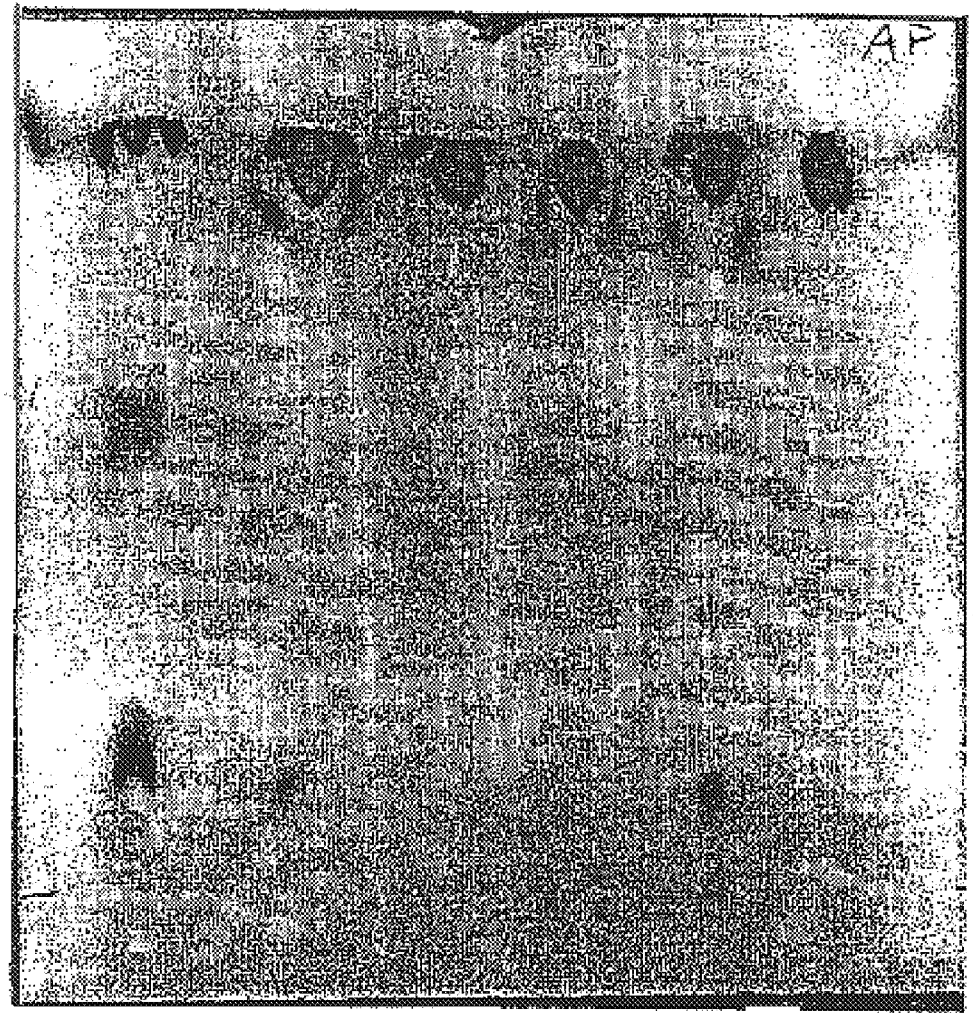
FIG. 16. Thin-layer chromatography of phospholipids of Angel Shark

Before describing the present invention in detail, it is to be understood that the invention is not limited in its application to the process details described herein. The invention is capable of other embodiments and of being practised in various ways. It is also to be understood that the phraseology or terminology used herein is for the purpose of description and not limitation.

The method of the invention comprises suspending freshly collected marine and aquatic material in acetone. Lipids are extracted with a ketone such as acetone. This allows a rapid dehydration of animal tissue and a migration of the lipid fraction to the solvent. The dry residue is a valuable product rich in active enzymes.

In a preferred embodiment, the extraction is carried out by successive acetone and alcohol treatments. Preferred alcohols are isopropanol, and t-butanol. The alcohol may also be substituted with an ester of acetic acid such as ethyl acetate. The procedure produces two successive lipid fractions and a dry residue enriched in protein, including active enzymes. Recovery of total lipids is comparable to the Folch et al. (1957) procedure reported in the background of the invention. It has been tested with krill, Calanus, fish and shark tissues.

Surprisingly, it was found that successive extraction treatments as proposed by the present invention has a better yield in lipid extraction that single solvent system extractions. The extraction using two successive solvents which starts with a ketone such as acetone is especially advantageous since the acetone, in effect, dehydrates the animal tissue. Having the animal tissue in dehydrated form greatly facilitates the extraction process with the second solvent, alcohol or an ester of acetic acid such as ethyl acetate.

In the case of zooplancton such as krill and Calanus and in the case of fish-filleting by-products such as fish viscera, it is noted that extraction with acetone alone may be sufficient to allow a cost-effective recovery of lipid fractions and separate recovery of a dry solid product rich in proteins including active enzymes.

The general extraction method of the present invention will now be described. The starting material consisting of freshly harvested and preferably finely divided marine and aquatic animal material is subjected to acetone extraction, for at about two hours and preferably overnight. However extraction time is not critical to the yield of lipid extraction. To facilitate extraction, it is preferable to use particles of less than 5 mm in diameter. Extraction is preferably conducted under inert atmosphere and at a temperature in the order of about 5° C. or less.

Preferably, the beginning of the extraction will be conducted under agitation for about 10 to 40 minutes, preferably 20 minutes. Although extraction time is not critical, it was found that a 2 hour extraction with 6:1 volume ratio of acetone to marine and aquatic animal material is best.

The solubilized lipid fractions are separated from the solid material by standard techniques including, for example, filtration, centrifugation or sedimentation. Filtration is preferably used.

After separation by filtration on an organic solvent resistant filter (metal, glass or paper) the residue is optionally washed with pure acetone, preferably two volumes (original volume of material) to recover yet more lipids. The combined filtrates are evaporated under reduced pressure. Optionally, flash evaporation or spray drying may be used. The water residue obtained after evaporation is allowed to separate from the oil phase (fraction I) at low temperature.

The solid residue collected on the filter is suspended and extracted with alcohol, such as ethanol, isopropanol, t-butanol or alternatively with ethyl acetate, preferably two volumes (original volume of material). The filtrate is evaporated leaving a second fraction of lipids (identified as fraction II). Although the extraction period is not critical, it was found that an extraction time of about 30 minutes is sufficient at temperatures below about 5° C.

Temperature of the organic solvents, except t-butanol, and temperature of the sample are not critical parameters, but it is preferable to be as cold as possible. However, in the case of t-butanol which is solid at room temperature, it is important to warm it before using it and to perform the extraction at 25° C. immediately.

Comparative Examples

To compare the efficiency of the extraction process, a classical technique (Folch et al. 1957) using chloroform and methanol was applied to krill. This method is the reference for measuring efficiency of the extraction process. Another comparison has been made with a technique using hexane as the extraction solvent. Lipid recovery by suspending lipid fractions in small volumes of their original solvents and measuring by gravimetry small aliquots after evaporation.

For all examples provided herein, the method of the present invention involving acetone extraction followed by extraction with a second solvent (ethyl acetate, for example) gave a translucent oil having appearance and properties more attractive than any oil obtained by the classical technique of Folch et al. (1957).

To analyze lipid composition, 780 µg of each extract was loaded on silica-gel plates and fractionated by thin layer chromatography, TLC (Bowyer et al. 1962) with the following solvents. Neutral lipids: hexane, ethyl ether, acetic acid (90:10:1, v/v) and phospholipids: chloroform, methanol, water (80:25:2, v/v). Fatty acid composition of *E. pacifica* was analyzed by gas liquid chromatography, GLC (Bowyer et al. 1962) including some modifications to the original technique: 2 h at 65° C. instead of 1 h at 80° C., three washes with hexane instead of two and no wash with water.

To get rid of traces of organic solvents, lipid fractions I and II are warmed to about 125° C. for about 15 minutes under inert atmosphere.

Fat was analyzed according to the American Oil Chemist's Society (AOCS). The following criteria have been used to analyze the lipids extracted: saponification and Wijs iodine indexes and moisture-volatile matter levels. Cholesterol content has also been determined by the method of Plummer 1987. The same analyzes and others have been made by an independent laboratory under Professor Robert Ackman's supervision (Canadian Institute of Fisheries Technology, DalTech, Dalhousie University, Halifax, Nova Scotia, Canada). This includes Wijs iodine index, peroxide and anisidine values, lipid class composition, fatty acid composition, free fatty acid FAME, cholesterol. tocopherol, all-trans retinol, cholecalciferol, astaxanthin and canthaxantin contents. Table 1 shows that higher levels of lipids are extracted from dry krill by acetone followed by ethanol as compared to the classical procedure of Folch et al. (1957).

Table 2 shows the results of lipid extraction from frozen *Euphausia pacifica*, a species of krill from Pacific Ocean. Assuming an eighty percent content of water, the lipid content is comparable to dry krill as shown in Table 1. Isopropanol, t-butanol and ethyl acetate, as solvent for the second extraction, give a yield less important than ethanol, but are not necessarily less effective in lipid recovery since ethanol carries more impurities than isopropanol, t-butanol or ethyl acetate. Then, they can be used as second solvent after acetone as well. Variations between results from acetone extractions are mainly due to the water-oil separations. These separations are influenced by the quantity of residual acetone in the water-oil solution after acetone evaporation. This quantity of acetone varies from an experiment to another, because the evaporation system used at a small scale is less reproducible (at the industrial scale, the evaporation step will be optimized). Single solvents have also been tested to extract the totality of lipids from krill. This shows that ethyl acetate (1,37% extraction rate), as hexane (0,23% extraction rate) are not good solvents, compared to acetone alone (1,86% extraction rate, and even greater extraction rates with an efficient acetone evaporation system).

One of the main advantages of the procedure is the removal of bacteria from extracts (lipid fraction and solid protein-rich material). Indeed, samples of *E. pacifica* incubated in different ratios of acetone at 4° C. for 112 days have been inoculated on NA medium containing Bacto™ beef extract 0,3%, Bacto™ peptone 0,5% and Bacto™ agar 1,5% (Difco Laboratories, Detroit, USA) then incubated at room temperature or 4° C. for 18 days. No significant bacterial growth was observed at a ratio of 1 volume of acetone per gram of krill. At higher proportions of acetone (2 volumes and 5 volumes), there was no bacterial growth at all, which means that acetone preserves krill samples. Acetone is known as an efficient bactericidal and viricidal agent (Goodman et al. 1980).

Table 3 shows the yield of lipids from *M. norvegica*. The percentage of lipids (3,67%) is comparable to the one obtained with *E. pacifica* (3,11%) shown in Table 2. Variations can be attributable to diet and time (season) of collection, which are different for those two species.

Table 4 shows the influence of grinding on the efficiency of extraction of *M. norvegica* lipids. These extractions were carried out under optimal conditions and show the definite advantage of the procedure over the classical method (4,46% versus 3,30%). It also shows that grinding may be an important factor when the species is large (4,46% versus 3,53%).

Table 5 reports on lipid extraction from Calanus. Considerable quantities of lipids were obtained. Some variations in Calanus species composition may explain the variations between experiments 1 and 2 (8,22% and 10,90% of fresh weight).

Tables 6–8 report the total amount of lipids extracted from fish tissue. The method of the present invention was demonstrated on mackerel, trout and herring. The method was demonstrated on peripheral tissues (mainly muscles) and viscera. Advantageously, the present method would permit the recovery of valuable lipid fractions from parts of fish that are usually wasted after the withdrawal of fillets of the fish. Those fish tissues not used after the transformation of the fish for human consumption could be stored in acetone, and lipids extracted therefrom in accordance with the present invention even if the method Folch [1957] recovers more lipid than our method. Indeed small amounts of lipids from mackerel (0.52% from viscera and 1,45% from tissues) have been extracted by the method of Folch after a first extraction with acetone and ethanol as described in the present invention. Comparative extractions with the method described in the present invention carried out in parallel with the method of Folch on trout and herring show superior recovery with the latter. However, it is noteworthy that the Folch method can not be applied for the recovery of lipids for commercial uses (because of toxicity).

In Tables 9 to 11, are shown results of lipids extraction from shark liver tissues. There is no marked difference in results between techniques within a species.

Tables 12 shows some characteristics features of fraction I (acetone) and fraction II (alcohol or ethyl acetate) for krill oil (*e. pacifica*). First, the saponification index of fraction I (130,6) indicates that this fraction contains fatty acids with longer chains, compared to fraction II (185,7). The Wijs iodine index of fraction I shows that this fraction contains high levels of polyunsaturated fatty acids. As compared to olive oil which has an index of 81.1. It explains why fraction I is liquid at room temperature. It is well known that unsaturated fatty acids have a fusion point inferior to the one of their saturated homologues. The same observations are made for fraction II which has a iodine index of 127,2. The fatty acid composition shown in Table 14 corroborates these iodine indexes: fraction I has a high percentage (30,24%) of polyunsaturated fatty acids (pentaenes+hexaenes) and so fraction II (22,98%). Finally, Table 12 shows also that fraction I is comprised of 10,0% of volatile matter and humidity after evaporation of the solvent. For the same test, the fraction II gives a value of 6,8%. To get rid of traces of solvents, it is important to briefly heat (to about 125° C., for about 15 min) the oil under nitrogen.

Results on krill oils obtained in accordance with the method of the present invention (fraction I extracted with acetone and fraction II extracted with ethyl acetate) are provided in Tables 12, 13, 14, 15, 16 and 17. It is noteworthy to mention that in Table 17, the carotenoids content was significantly high as measured in terms of two carotenoids namely astaxanthin and canthaxanthin. Indeed, duplicates analyzes revealed values of 92 to 124 µg/g of lipid fraction for astaxanthin and 262 to 734 µg/g for canthaxanthin. Thus, for the purpose of the present invention it may be said that the krill extract comprises astaxanthin at least 75 and preferably at least 90 ug/g of lipid fraction. In the case of canthaxanthin, at least 250 and preferably at least 270 µg/g of lipid fraction. Low values for peroxide and anisidine are advantageous and are due to the presence of high levels of natural antioxidants (astaxanthin and canthaxanthin). These compounds are indicative of favourable pharmaceutical or cosmetological properties of the krill extract whereby high levels of carotenoids indicate excellent transdermal migration characteristics. Thus, krill extract is a good candidative for transdermal delivery of medicines.

Table 18 shows the best mode of the method in accordance with the present invention for lipid extraction of aquatic animal tissues.

Table 19 shows that the enzyme activity of the solid fraction is maintained following the method of the present invention. Indeed, the demonstration was completed for solid krill residue obtained after successive acetone and ethyl acetate extraction. Proteolytic activities were measure by the liberation of amino groups by spectrophotometric assay using o-pthaldialdehyde as reagent. Protein concentrations were measured by the Bradford method. Soluble proteins were extracted with water and added to a 10% lactoserum protein concentrate obtained by ultrafiltration. At the end of incubation at 37° C. in 50 mM potassium phosphate buffer, trichloroacetic acid was added and the amount of $NH_3$ group was measured in the supernatant according to the method of Church et al. [1983, J Dairy Sci 66: 1219–1227].

FIGS. 1 to 6 show chromatograms of fatty acid composition of E. pacifica lipids. On each of them, high proportions of 20:5 and 22:6 fatty acids (characteristic of marine and aquatic oils) are noticeable and represented by two distinct peaks.

Variations in lipid patterns of neutral lipids (from FIG. 7 to FIG. 11) from one species to another are attributable to the differences in food sources. Within a species (E. pacifica, for example) there is no marked variation between lipid patterns obtained from different techniques of lipid extraction. Concerning phospholipids (FIG. 12 to FIG. 16), the opposite is observed: variations are explained by the different extraction processes of lipids since the same species do not lead to the same lipid pattern. Lipids from shark species (extracted by the mentioned methods) and commercial cod-liver oil (sample available from Uniprix drugstores, Province of Québec, Canada) are mainly composed of neutral lipids as opposed to phospholipids.

Figure 17:
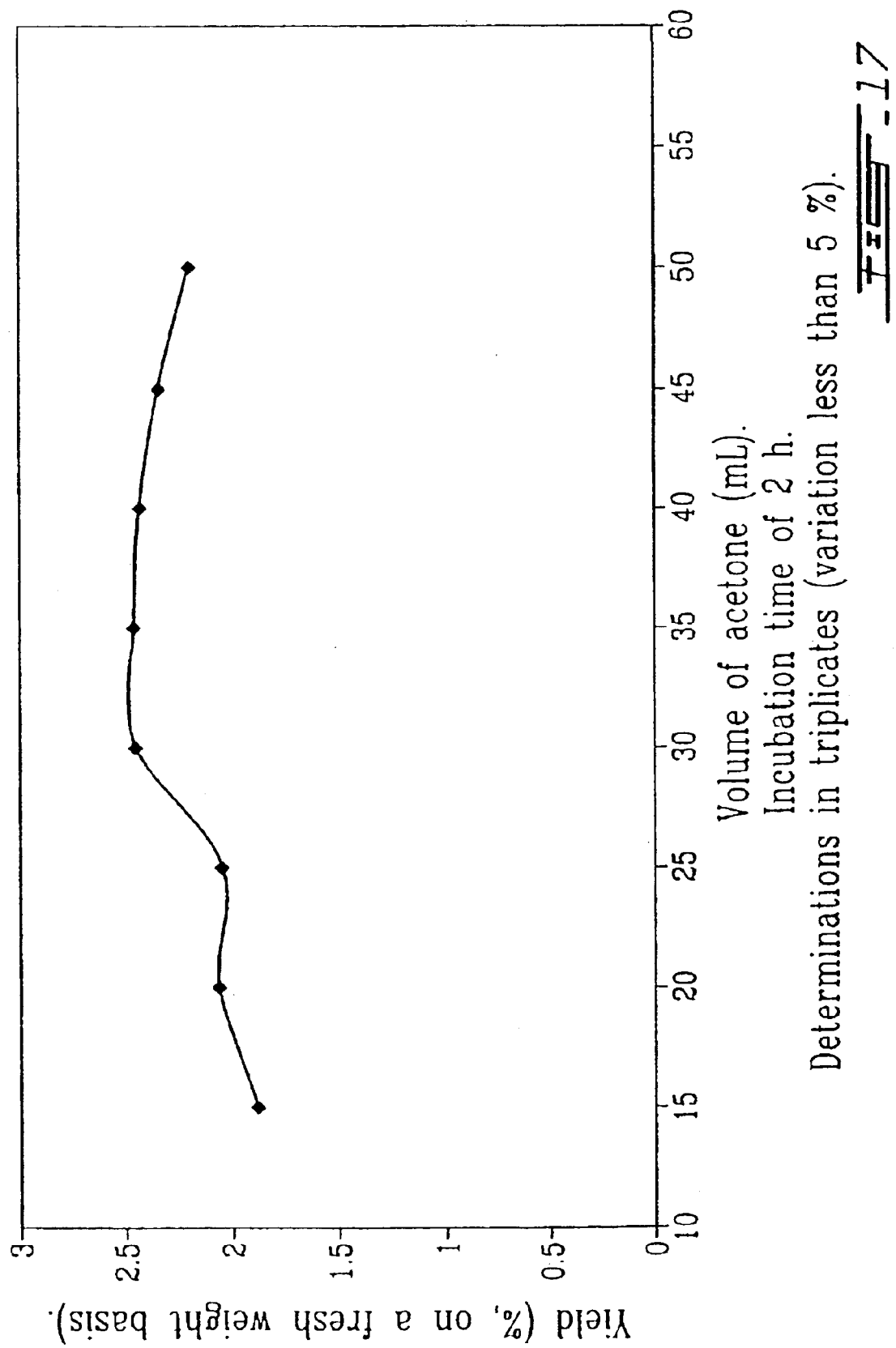
FIG. 17. Influence of the volume of acetone on lipid extraction (*E. pacifica*)
Figure 18:
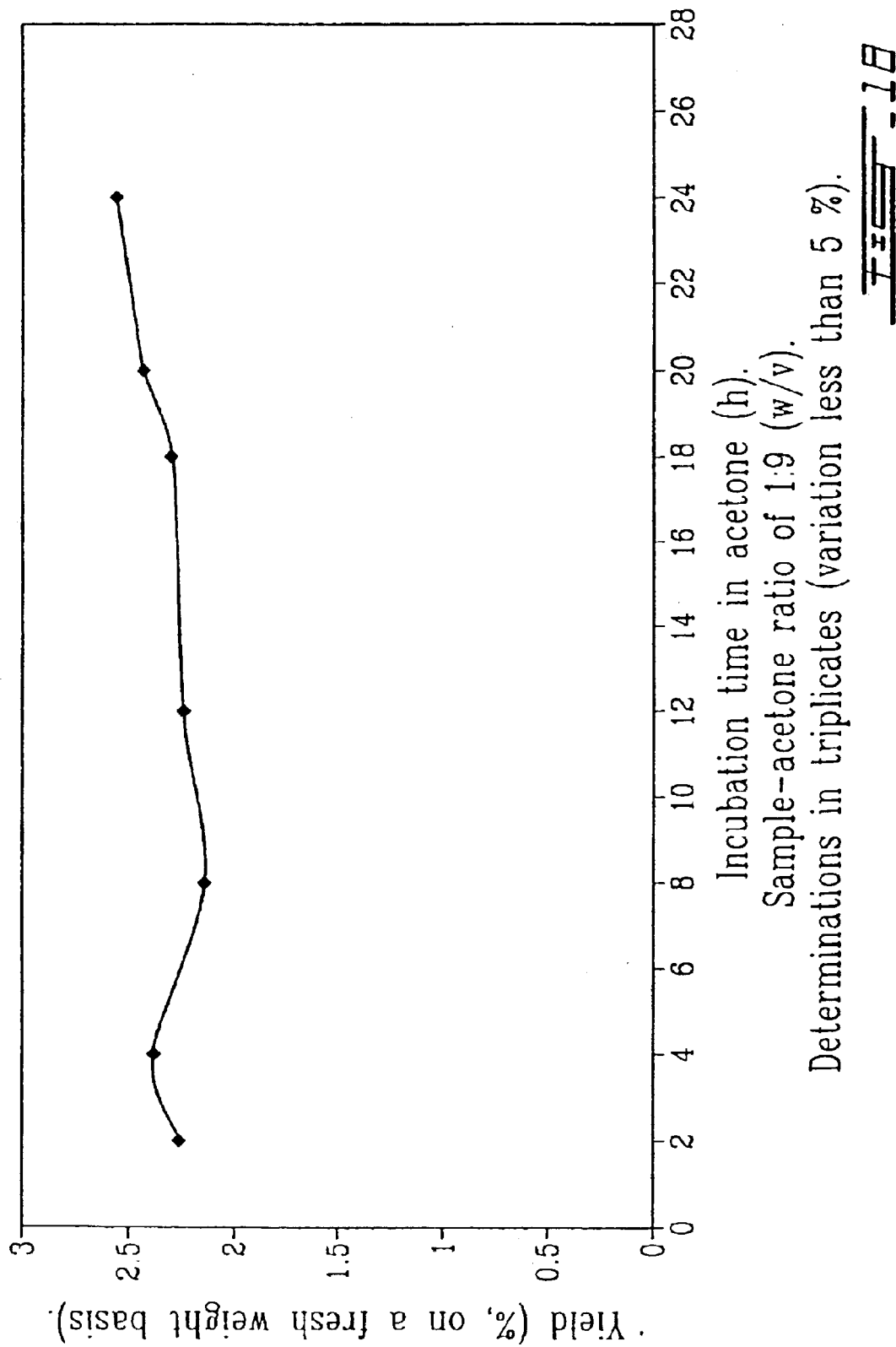
FIG. 18. Influence of incubation time in acetone on lipid extraction (*E. pacifica*)
Figure 19:
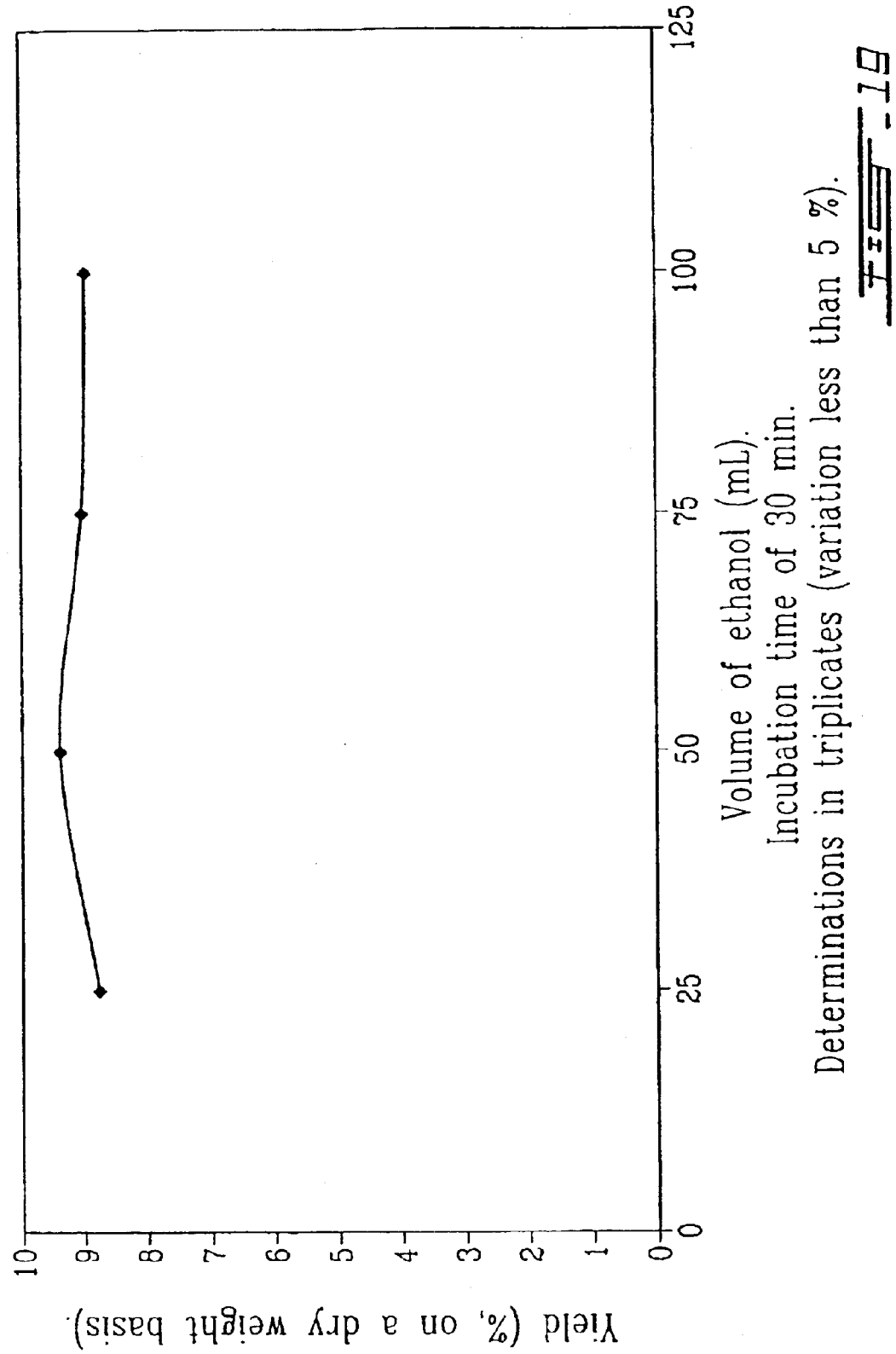
FIG. 19. Influence of the volume of ethanol on lipid extraction (*E. pacifica*)
Figure 20:
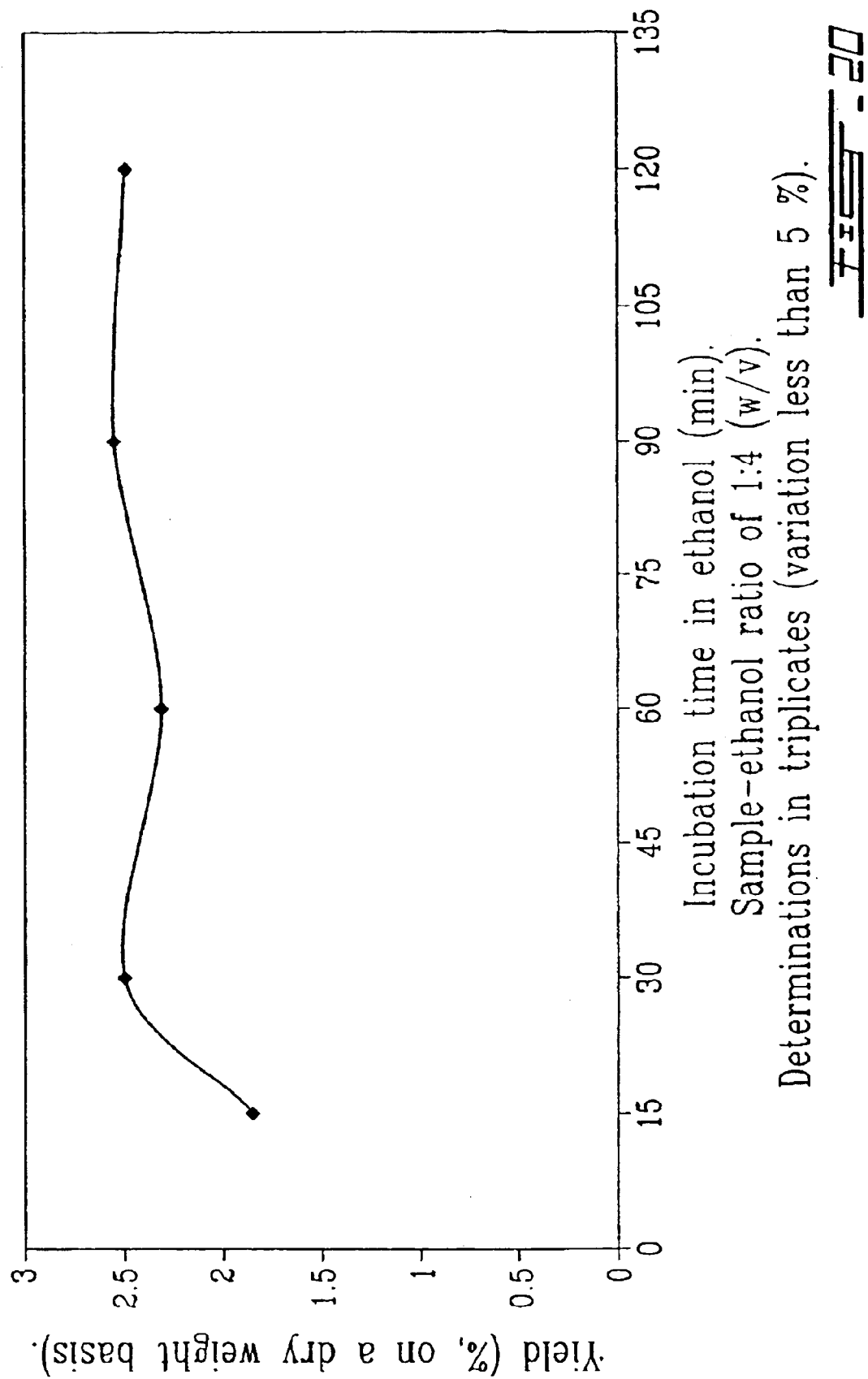
FIG. 20. Influence of incubation time in ethanol on lipid extraction (*T. raschii*)

The influence of the volume of solvent and incubation time on the efficiency of the acetone to extract lipids from E. pacifica is illustrated in FIGS. 17 and 18, respectively. A ratio of 1:6 (w/v) produced optimal yield with near complete extraction after 2 h. The second extraction step has been experimented with ethanol. The volume of this solvent does not appear to be critical since the same yield was obtained with different volumes of ethanol (FIG. 19), but incubations time in ethanol should be at least 30 minutes as indicated by the results on FIG. 20.

One of the inventors, Dr. Adrien Beaudoin, has ingested the different lipid fractions of krill. No side effect profile was observed.

Although the invention has been described above with respect with one specific form, it will be evident to a person skilled in the art that it may be modified and refined in various ways. It is therefore wished to have it understood that the present invention should not be limited in scope, except by the terms of the following claims.

Demonstration that krill residue, obtained after acetone and ethyl acetate extraction, contains enzyme proteolytic activities. Proteolytic activities were measured by the liberation of amino groups by spectrophotometric assay using o-phthaldialdehyde as reagent. Protein concentrations were measured by the Bradford method.

The enzyme source was the residue obtained after acetone and ethyl acetate extractions of lipids. Soluble proteins were extracted with water and added to a 10% lactoserum protein concentrate obtained by ultrafiltration.

At the end of incubation at 37° C. in 50 mM potassium phosphate buffer, trichloroacetic acid was added and the amount of $NH_3$ groups were measured in the supernatant according to Church and al. 1983.

BIBLIOGRAPHY

Bowyer, D. E., Leat, W. M. F., Howard, A. N. and Gresham, G. A. 1962. The determination of the fatty acid composition of serum lipids separated by thin-layer chromatography; and a comparison with column chromatography. BBA. 70: 423–431.

Chandrasekar, B., Troyer, D. A., Venkatraman, J. T. and Fernandes, G. 1996. Tissue specific regulation of transforming growth factor beta by omega-3 lipid-rich krill oil in autoimmune murine lupus. Nutr Res. 16(3): 489–503.

Christensen, M. S., Hoy, C-E. and Redgrave, T. G. 1994. Lymphatic absorption of n-3 polyunsaturated fatty acids from marine oils with different intramolecular fatty acid distributions. BBA. 1215: 198–204.

Church, F. C., Swaisgood, H. E., Porter, D. H. and Catignani, G. L. 1983. Spectrophotometric assay using o-Phthaldialdehyde for determination of proteolysis in milk and isolated milk proteins. J Dairy Sci. 66: 1219–1227.

Difco laboratories. 1984. Difco Manual Dehydrated Culture Media and Reagents for Microbiology. 10$^{th}$ ed. Detroit.

Folch, J., Lees, M. and Sloane-Stanley, G. H. 1957. A simple method for the isolation and purification of total lipids from animal tissues. J. biol. Chem. 226: 497–509.

Goodman Gilman, A., Goodman, L. L. and Gilman, A. 1980. The Pharmacological Basis of Therapeutics. 6$^{th}$ ed. Collier Macmillan Canada ltd, Toronto.

Harwood, H. J. and Geyer, R. P. 1964. Biology Data Book. The Federation of American Societies for Experimental Biology, Washington.

Heligren, L., Karlstam, B., Mohr, V. and Vincent, J. 1991. Krill enzymes. A new concept for efficient debridement of necrotic ulcers. Int J Dermatol. 30(2): 102–103 Plummer, D. T. 1987. An introduction to practical biochemistry. 3$^{th}$ ed. McGraw-Hill Book Company, London.

Rawn, J. D. 1990. Traité de biochimie. De Boeck-Wesmael, Bruxelles.

Runge, J. A. and Joly, P. 1994. Rapport sur l'état des invertébrés en 1994: 7:0 Zooplancton (Euphausiacés et Calanus) de l'Estuaire et du Golfe du Saint-Laurent Sargent, J. R. 1997. Fish oils and human diet. Br J Nutr.78 Suppl 1: S5–S13.

TABLE 1

EXTRACTION OF DRY KRILL LIPIDS (*E. pacifica*)

| Exp. No. | Technique | Yield (%) | Total (%) | Mean (%) ± s.d. |
|---|---|---|---|---|
| 1- | acetone[a] | 8.00 | | |
| | ethanol[b] | 7.60 | 15.60 | |
| 2- | acetone[a] | 19.70 | | |
| | ethanol[b] | 6.90 | 26.60 | |
| 3- | acetone[a] | 8.15 | | |
| | ethanol[b] | 11.20 | 19.35 | |
| 4- | acetone[a] | 6.80 | | |
| | ethanol[b] | 13.60 | 20.40 | |
| | | | | 20.49 ± 3.95 |
| 5- | chlor:MeOH[c] | | 15.50 | |
| 6- | " | | 14.90 | |
| | | | | 15.20 ± 0.30 |

Determinations in triplicates (variation <5%).
[a]Extraction made with a sample-solvent ratio of 1:9 (w/v), no incubation.
[b]Extraction made with a sample-solvent ratio of 1:4 (w/v), incubated 1 night at 4° C., following a first extraction with acetone.
[c]Folch et al. 1957.

TABLE 2

EXTRACTION OF FROZEN KRILL LIPIDS (*E. pacifica*)

| Exp. No. | Technique | Yield (%) | Total (%) | Mean (%) ± s.d. |
|---|---|---|---|---|
| 1- | acetone[a] | 1.17 | | |
| | ethanol[b] | 1.23 | 2.40 | |
| 2- | acetone[a] | 3.05 | | |
| | ethanol[b] | 1.09 | 4.14 | |
| 3- | acetone[a] | 1.53 | | |
| | ethanol[b] | 1.26 | 2.79 | |
| | | | | 3.11 ± 0.91 |
| 4- | acetone[a] | 2.45 | | |
| | isopropanol[b] | 0.70 | 3.15 | |
| 5- | acetone[a] | 1.80 | | |
| | isopropanol[b] | 0.80 | 2.60 | |
| 6- | acetone[a] | 1.60 | | |
| | isopropanol[b] | 0.80 | 2.40 | |
| | | | | 2.27 ± 0.39 |
| 7- | acetone[a] | 2.15 | | |
| | t-butanol[c] | 0.47 | 2.62 | |
| 8- | acetone[a] | 2.11 | | |
| | t-butanol[c] | 0.40 | 2.51 | |
| 9- | acetone[a] | 2.37 | | |
| | t-butanol[c] | 0.45 | 2.82 | |
| | | | | 2.65 ± 0.16 |
| 10- | acetone[a] | 2.28 | | |
| | ethyl acetate[b] | 0.21 | 2.49 | |
| 11- | acetone[a] | 1.09 | | |
| | ethyl acetate[b] | 0.16 | 1.25 | |
| 12- | acetone[a] | 2.54 | | |
| | ethyl acetate[b] | 0.09 | 2.63 | |
| | | | | 2.12 ± 0.76 |
| 13- | combined acetone-ethanol[d] | | 3.28 | |
| 14- | combined acetone-ethanol[d] | 3.02 | | |
| 15- | combined acetone-ethanol[d] | 3.25 | | |
| | | | | 3.18 ± 0.14 |
| 16- | ethyl acetate[e] | 1.32 | | |
| 17- | " | 1.49 | | |
| 18- | " | 1.31 | | |
| | | | | 1.37 ± 0.10 |
| 19- | hexane[e] | 0.31 | | |
| 20 | " | 0.18 | | |
| 21- | " | 0.20 | | |
| | | | | 0.23 ± 0.07 |
| 22- | chlor:MeOH[f] | 2.37 | | |
| 23- | " | 2.07 | | |
| 24- | " | 2.62 | | |
| | | | | 2.35 ± 0.28 |

Determinations in triplicates (variation <5%).
[a]Extraction made with a sample-solvent ratio of 1:6 (w/v), incubated 2 h at 4° C.
[b]Extraction made with a sample-solvent ratio of 1:2 (w/v), incubated 30 min at 4° C., following a first extraction with acetone.
[c]Extraction made with a sample-solvent ratio of 1:2 (w/v), incubated 30 min at 25° C., following a first extraction with acetone.
[d]Extraction made with a sample-acetone-ethanol ratio of 1:5:5 (w/v/v), incubated 2 h at 4° C.
[e]Extraction made with a sample-solvent ratio of 1:9 (w/v), incubated 2 h at 4° C.
[f]Folch et al. 1957.

TABLE 3

EXTRACTION OF FROZEN KRILL LIPIDS (*M. norvegica*)

| Exp. No. | Technique | Yield (%) | Total (%) | Mean (%) ± s.d. |
|---|---|---|---|---|
| 1- | acetone[a] | 1.82 | | |
| | ethanol[b] | 1.82 | 3.64 | |
| 2- | acetone[a] | 1.15 | | |
| | ethanol[b] | 2.35 | 3.50 | |
| 3- | acetone[a] | 1.68 | | |
| | ethanol[b] | 2.19 | 3.87 | |
| | | | | 3.67 ± 0.15 |

Determinations in triplicates (variation <5%).
[a]Extraction made with a sample-solvent ratio of 1:9 (w/v), incubated 1 night at 4° C.
[b]Extraction made with a sample-solvent ratio of 1:4 (w/v), incubated 1 h at 4° C., following a first extraction with acetone.

TABLE 4

INFLUENCE OF GRINDING ON EXTRACTION OF FROZEN KRILL LIPIDS (*M. norv gica*)

| Exp. No. | Technique | Krill ground before 1st extraction | Yield (%) | Total (%) |
|---|---|---|---|---|
| 1- | acetone[a] | yes | 3.10 | |
| | ethanol[b] | | 1.07 | 4.17 |
| 2- | acetone[a] | no | 2.14 | |
| | ethanol[b] | | 1.39 | 3.53 |
| 3- | acetone[a] | yes | 3.32 | |
| | ethanol[b] | | 1.14 | 4.46 |
| 4- | chlor:MeOH[c] | yes | 3.30 | |
| 5- | " | yes | 3.26 | |

Determinations in triplicates (variation <5%).
[a]Extraction made with a sample-solvent ratio of 1:6, incubated 2 h at 4° C.
[b]Extraction made with a sample-solvent ratio of 1:2, incubated 30 min at 4° C., following a first extraction with acetone.
[c]Folch et al. 1957.

TABLE 5

EXTRACTION OF FROZEN Calanus LIPIDS (Calanus sp.)

| Exp. No. | Technique | Yield (%) | Total (%) | Mean (%) ± s.d. |
|---|---|---|---|---|
| 1- | acetone[a] | 6.18 | | |
| | ethanol[b] | 2.04 | 8.22 | |
| 2- | acetone[a] | 8.64 | | |
| | ethanol[b] | 2.26 | 10.90 | |
| | | | | 9.56 ± 1.34 |

Determinations in triplicates (variation <5%).
[a]Extraction made with a sample-solvent ratio of 1:9 (w/v), incubated 1 night at 4° C.
[b]Extraction made with a sample-solvent ratio of 1:4 (w/v), incubated 1 h at 4° C., following a first extraction with acetone.

TABLE 6

EXTRACTION OF FRESH FISH LIPIDS (Macker I)

| Exp. No. | Technique | Yield (%) | Total (%) |
|---|---|---|---|
| 1- viscera fish 1 | acetone[a] ethanol[b] | 6.11 0.59 | 6.70 |
| 2- tissues fish 1 | acetone[a] ethanol[b] | 3.78 0.91 | 4.69 |
| 3- viscera fish 2 | acetone[a] ethanol[b] | 10.46 0.57 | 11.03 |
| 4- tissues fish 2 | acetone[a] ethanol[b] | 6.65 1.41 | 8.06 |
| 5- viscera fish 3 | acetone[a] ethanol[b] | 8.39 0.66 | 9.05 |
| 6- tissues fish 3 | acetone[a] ethanol[b] | 5.27 0.97 | 6.24 |
| 7- viscera fish 4 | acetone[a] ethanol[b] | 8.47 0.69 | 9.16 |
| 8- tissues fish 4 | acetone[a] ethanol[b] | 8.40 1.02 | 9.42 |
| 9- viscera fish 1 | chlor:MeOH[c] | | 0.52 |
| 10- tissues fish 1 | " | | 1.45 |

[a]Extraction made with a sample-solvent ratio of 1:9 (w/v), incubation time:
fish 1 viscera: 4 h, fish 1 tissues: 23 h
fish 2 viscera: 23 h 45, fish 2 tissues: 45 h 30
fish 3 viscera: 8 days 2 h 20, fish 3 tissues: 8 days 22 h 30
fish 4 viscera: 17 days 23 h, fish 4 tissues: 18 days 2 h 25.
[b]Extraction made with a sample-solvent ratio of 1:4 (w/v), incubated 1 h at 4° C., following a first extraction with acetone.
[c]Folch et al. 1957, following extractions with acetone, then ethanol.

TABLE 7

EXTRACTION OF FRESH FISH LIPIDS (Trout)

| Exp. No. | Technique | Yield (%) | Total (%) |
|---|---|---|---|
| 1- viscera | acetone[a] | 34.70 | |
| | ethanol[b] | 2.18 | 36.88 |
| 2- tissues | acetone[a] | 5.53 | |
| | ethanol[b] | 1.17 | 6.70 |
| 3- viscera | chlor:MeOH[c] | | 39.81 |
| 4- tissues | " | | 14.93 |

Determinations in triplicates (variation <5%).
[a]Extraction made with a sample-solvent ratio of 1:9 (w/v), incubated 1 night at 4° C.
[b]Extraction made with a sample-solvent ratio of 1:4 (w/v), incubated 1 h at 4° C., following a first extraction with acetone.
[c]Folch et al. 1957.

TABLE 8

EXTRACTION OF FRESH FISH LIPIDS (Herring)

| Exp. No. | Technique | Yield (%) | Total (%) |
|---|---|---|---|
| 1- tissues and viscera | acetone[a] ethanol[b] | 2.09 0.68 | 2.77 |
| 2- tissues and viscera | chlor:MeOH[c] | | 5.95 |

Determination in triplicates (variation <5%).
[a]Extraction made with a sample-solvent ratio of 1:9 (w/v), incubated 1 night at 4°.
[b]Extraction made with a sample-solvent ratio of 1:4 (w/v), incubated 1 h at 4° C., following a first extraction with acetone.
[c]Folch et al. 1957.

TABLE 9

EXTRACTION OF FRESH SHARK LIVER LIPIDS (*M. schmitti*)

| Exp. No. | Technique | Yield (%) | Total (%) |
|---|---|---|---|
| 1- | acetone[a] | 36.39 | |
| | ethyl acetate[b] | 4.48 | 40.87 |

TABLE 9-continued

EXTRACTION OF FRESH SHARK LIVER LIPIDS (*M. schmitti*)

| Exp. No. | Technique | Yield (%) | Total (%) |
|---|---|---|---|
| 2- | ethyl acetate[c] | | 36.68 |
| 3- | chlor:MeOH[d] | | 41.86 |

Determinations in triplicates (variations <5%).
[a]Extraction made with a sample-solvent ratio of 1:9 (w/v), incubated 2 h at 4° C.
[b]Extraction made with a sample-solvent ratio of 1:2 (w/v), incubated 30 min at 4° C., following a first extraction with acetone.
[c]Extraction made with a sample-solvent ratio of 1:9 (w/v), incubated 2 h at 4° C.
[d]Folch et al. 1957.

TABLE 10

EXTRACTION OF FRESH SHARK LIVER LIPIDS (*G. galeus*).

| Exp. No. | Technique | Yield (%) | Total (%) |
|---|---|---|---|
| 1- | acetone[a] | 21.39 | |
|  | ethyl acetate[b] | 5.27 | 26.66 |
| 2- | ethyl acetate[c] | | 25.89 |
|  | chlor:MeOH[d] | | 29.99 |

Determinations in triplicates (variations <5%).
[a]Extraction made with a sample-solvent ratio of 1:9 (w/v), incubated 2 h at 4° C.
[b]Extraction made with a sample-solvent ratio of 1:2 (w/v), incubated 30 min at 4° C., following a first extraction with acetone.
[c]Extraction made with a sample-solvent ratio of 1:9 (w/v), incubated 2 h at 4° C.
[d]Folch et al. 1957.

TABLE 11

EXTRACTION OF FRESH SHARK LIVER LIPIDS (Angel Shark)

| Exp. No. | Technique | Yield (%) | Total (%) |
|---|---|---|---|
| 1- | acetone[a] | 19.23 | |
|  | ethyl acetate[b] | 8.98 | 28.21 |
| 2- | ethyl acetate[c] | | 39.22 |
|  | chlor:MeOH[d] | | 39.23 |

Determinations in triplicates (variations <5%).
[a]Extraction made with a sample-solvent ratio of 1:9 (w/v), incubated 2 h at 4° C.
[b]Extraction made with a sample-solvent ratio of 1:2 (w/v), incubated 30 min at 4° C., following a first extraction with acetone.
[c]Extraction made with a sample-solvent ratio of 1:9 (w/v), incubated 2 h at 4° C.
[d]Folch et al. 1957.

TABLE 12

CHARACTERISTICS OF KRILL OIL (*E. pacifica*)

| | independent laboratory[a] | handbook[b] |
|---|---|---|
| Saponification index | | |
| Fraction I[c] | 130.6 | — |
| Fraction II[d] | 185.7 | — |
| Olive oil | 192.0[e] | 189.7 |
| Wijs iodine index | | |
| Fraction I[c] | 185.2 | 172.5 |
| Fraction II[d] | 127.2 | 139.2 |
| Olive oil | 85.3[e] | 81.1 |

TABLE 12-continued

CHARACTERISTICS OF KRILL OIL (*E. pacifica*)

| | independent laboratory[a] | handbook[b] |
|---|---|---|
| Cholesterol content (%) | | |
| Fraction I[c] | 2.1 | 1.9 | 
| Fraction II[d] | 3.7 | 3.0 |
| Olive oil | 0.2[e] | — |
| Volatile matter and moisture levels (%) | | |
| Fraction I[c] | 10.0 | — |
| Fraction II[d] | 6.8 | — |
| Peroxide value (meq peroxide/kg oil) | | |
| Fraction I[c] | — | 0.0 |
| Fraction II[d] | — | 0.0 |
| p-Anisidine value ($g^{-1}$ absorption) | | |
| Fraction I[c] | — | 0.1 |
| Fraction II[d] | — | 5.5 |

[a]Professor Robert Ackman's laboratory, Canadian Institute of Fisheries Technology, Halifax, Nova Scotia.
[b]Harwood and Geyer 1964.
[c]Extraction made with a sample-acetone ratio of 1:6 (w/v), incubated 2 h at 4° C.
[d]Extraction made with a sample-ethyl acetate ratio of 1:2 (w/v), incubated 30 min at 4° C., following a first extraction with acetone.
[e]Extra virgin olive oil cold compressed from Bertolli ™.

TABLE 13

LIPID CLASS COMPOSITION OF KRILL OIL (AREA %) (*E. pacifica*)

| | |
|---|---|
| Triglycerides | |
| Fraction I[a] | 19.0 ± 0.7 |
| Fraction II[b] | 66.5 ± 2.3 |
| Hydrocarbons | |
| Fraction I[a] | trace |
| Fraction II[b] | 1.3 ± 0.1 |
| Free fatty acids | |
| Fraction I[a] | 23.7 ± 1.1 |
| Fraction II[b] | 20.3 ± 0.3 |
| Monoglycerides | |
| Fraction I[a] | 1.4 ± 0.3 |
| Fraction II[b] | 0.5 ± 0.1 |
| Phospholipids or other polar material | |
| Fraction I[a] | 54.1 ± 6.1 |
| Fraction II[b] | 8.5 ± 1.6 |

Data from Professor Robert Ackman's laboratory, Canadian Institute of Fisheries Technology, Halifax, Nova Scotia.
[a]Extraction made with a sample-acetone ratio of 1:6 (w/v), incubated 2 h at 4° C.
[b]Extraction made with a sample-ethyl acetate ratio of 1:2 (w/v), incubated 30 min at 4° C., following a first extraction with acetone.

TABLE 14

FATTY ACID COMPOSITION OF KRILL OIL (WT/WT %) (*E. pacifica*)

| Fatty acids | Fraction I[a] | Fraction II[b] |
|---|---|---|
| 12:0 | 0.0 | 0.1 |
| 13:0 | 0.2 | 0.1 |

TABLE 14-continued

FATTY ACID COMPOSITION OF KRILL OIL (WT/WT %) (E. pacifica)

| Fatty acids | Fraction I[a] | Fraction II[b] |
|---|---|---|
| ISO 14:0 | 0.4 | 0.6 |
| 14:0 | 4.2 | 7.6 |
| ISO 15:0 | 0.5 | 0.7 |
| ANT 15:0 | 0.2 | 0.2 |
| 15:0 | 0.6 | 1.0 |
| ISO 16:0 | 0.2 | 0.3 |
| ANT 16:0 | 0.2 | 0.2 |
| 16:0 | 14.1 | 21.6 |
| 7MH | 0.6 | 0.9 |
| ANT 17:0 | 0.1 | 0.3 |
| 17:0 | 2.8 | 3.7 |
| 18:0 | 1.0 | 1.6 |
| 20:0 | 0.1 | 0.3 |
| Saturates | 25.2 | 39.2 |
| 14:1 | 0.4 | 0.5 |
| 15:1 | 0.1 | 0.2 |
| 16:1 n-7 | 6.6 | 7.8 |
| 16:1 n-5 | 0.6 | 0.2 |
| 17:1 | 0.6 | 0.7 |
| 18:1 n-9 | 8.0 | 9.8 |
| 18:1 n-7 | 4.2 | 5.6 |
| 18:1 n-5 | 0.1 | 0.1 |
| 20:1 n-9 | 0.3 | 0.4 |
| 20:1 n-7 | 0.3 | 0.4 |
| 20:1 n-5 | 0.3 | 0.4 |
| 22:1 n-11 + 13 | 0.1 | 0.2 |
| Monoenes | 21.6 | 26.3 |
| 16:2 n-6 | 0.6 | 1.2 |
| 16:2 n-4 | 1.3 | 1.3 |
| 18:2 n-7 | 0.1 | 0.2 |
| 18:2 n-6 | 2.0 | 1.8 |
| 18:2 n-4 | 0.1 | 0.1 |
| 20:2 NMID | 0.2 | 0.2 |
| 20:2 n-6 | 0.1 | 0.1 |
| Dienes | 4.4 | 4.9 |
| 16:3 n-4 | 1.4 | 1.2 |
| 18:3 n-6 | 0.4 | 0.3 |
| 18:3 n-4 | 0.2 | 0.2 |
| 18:3 n-3 | 3.2 | 3.0 |
| 18:3 n-1 | 0.1 | 0.1 |
| 20:3 n-3 | 0.1 | 0.1 |
| Trienes | 5.4 | 4.9 |
| 16:4 n-3 | 0.9 | 0.7 |
| 16:4 n-1 | 1.0 | 0.8 |
| 18:4 n-3 | 9.2 | 7.4 |
| 18:4 n-1 | 0.1 | 0.0 |
| 20:4 n-6 | 0.7 | 0.5 |
| 20:4 n-3 | 0.7 | 0.3 |
| Tetraenes | 12.6 | 9.7 |
| 20:5 n-3 | 17.4 | 8.6 |
| 21:5 n-3 | 0.7 | 0.5 |
| 22:5 n-6 | 0.2 | 0.1 |
| 22:5 n-3 | 0.5 | 0.3 |
| Pentaenes | 18.8 | 9.5 |
| 22:6 n-3 | 13.2 | 6.6 |
| Hexaenes | | |
| Iodine value calculated | 214.8 | 145.1 |

Data from Professor Robert Ackman's laboratory, Canadian Institute of Fisheries Technology, Halifax, Nova Scotia.
[a]Extraction made with a sample-acetone ratio of 1:6 (w/v), incubated 2 h at 4° C.
[b]Extraction made with a sample-ethyl acetate ratio of 1:2 (w/v), incubated 30 min at 4° C., following a first extraction with acetone.

TABLE 15

KRILL LIPID FREE FATTY ACID FAME (WT/WT %) (E. pacifica)

| Fatty acids | Fraction I[a] | Fraction II[b] |
|---|---|---|
| 12:0 | 0.5 | 0.1 |
| 13:0 | 0.2 | 0.0 |
| ISO 14:0 | 0.2 | 0.2 |
| 14:0 | 1.3 | 2.6 |
| ISO 15:0 | 0.3 | 0.3 |
| ANT 15:0 | 0.1 | 0.1 |
| 15:0 | 0.2 | 0.5 |
| ISO 16:0 | 0.1 | 0.2 |
| ANT 16:0 | 0.2 | 0.1 |
| 16:0 | 3.3 | 10.6 |
| 7MH | 0.6 | 0.8 |
| ANT 17:0 | 0.2 | 0.1 |
| Phytanic | 0.2 | 0.0 |
| 17:0 | 0.5 | 0.8 |
| 18:0 | 0.2 | 0.6 |
| 20:0 | 0.3 | 0.2 |
| 22:0 | 0.0 | 0.1 |
| Saturates | 8.4 | 17.4 |
| 14:1 | 0.2 | 0.2 |
| 15:1 | 0.2 | 0.1 |
| 16:1 n-9 | 0.5 | 0.0 |
| 16:1 n-7 | 5.2 | 6.8 |
| 16:1 n-5 + I 17:0 | 0.1 | 0.1 |
| 17:1 | 0.6 | 0.7 |
| 18:1 n-9 | 7.0 | 11.4 |
| 18:1 n-7 | 4.9 | 9.3 |
| 18:1 n-5 | 0.1 | 0.3 |
| 20:1 n-11 | 0.2 | 0.3 |
| 20:1 n-9 | 0.1 | 0.3 |
| 22:1 n-11 + 13 | 0.1 | 0.2 |
| 24:1 n-9 | 0.0 | 0.1 |
| Monoenes | 19.2 | 29.8 |
| 16:2 n-6 | 0.4 | 0.9 |
| 16:2 n-4 | 1.2 | 1.0 |
| 18:2 n-7 | 0.1 | 0.2 |
| 18:2 n-6 | 2.4 | 2.6 |
| 18:2 n-4 | 0.1 | 0.1 |
| 20:2 n-6 | 0.1 | 0.1 |
| Dienes | 4.3 | 4.9 |
| 16:3 n-3 + I 17:1 | 1.4 | 0.9 |
| 16:3 n-3 + I 18:0 | 0.2 | 0.5 |
| 18:3 n-6 | 0.4 | 0.3 |
| 18:3 n-4 | 0.1 | 0.1 |
| 18:3 n-3 | 3.3 | 3.4 |
| 18:3 n-1 | 0.1 | 0.1 |
| 20:3 n-6 | 0.1 | 0.1 |
| 20:3 n-3 | 0.1 | 0.2 |
| Trienes | 5.7 | 5.6 |
| 16:4 n-3 | 0.6 | 0.3 |
| 16:4 n-1 | 1.0 | 0.6 |
| 18:4 n-3 | 9.8 | 6.2 |
| 18:4 n-1 | 0.1 | 0.1 |
| 20:4 n-6 | 1.7 | 1.4 |
| 20:4 n-3 | 0.6 | 0.5 |
| 22:4 n-3 | 0.3 | 0.3 |
| Tetraenes | 14.1 | 9.4 |
| 18:5 n-3 | 0.2 | 0.1 |
| 20:5 n-3 | 26.4 | 17.4 |
| 21:5 n-3 | 0.9 | 0.6 |
| 22:5 n-6 | 0.0 | 0.1 |
| 22:5 n-3 | 0.7 | 0.5 |
| Pentaenes | 28.2 | 18.7 |
| 22:6 n-3 | 20.5 | 14.4 |
| Hexaenes | 20.5 | 14.4 |
| Iodine value calculated | 291.6 | 220.3 |

Data from Professor Robert Ackman's laboratory, Canadian Institute of Fisheries Technology, Halifax, Nova Scotia.
[a]Extraction made with a sample-acetone ratio of 1:6 (w/v), incubated 2 h at 4° C.
[b]Extraction made with a sample-ethyl acetate ratio of 1:2 (w/v), incubated 30 min at 4° C., following a first extraction with acetone.

TABLE 16

TOCOPHEROL, ALL-trans RETINOL AND CHOLECALCIFEROL CONTENT IN KRILL OIL (*E. pacifica*)

| alpha-tocopherol by HPLC (IU) | |
|---|---|
| Fraction I[a] | 0.91 |
| Fraction II[b] | 0.83 |
| gamma-tocopherol by HPLC µg/g | |
| Fraction I[a] | Tr |
| Fraction I[b] | Tr |
| delta-tocopherol by HPLC µg/g | |
| Fraction I[a] | N.D. |
| Fraction II[b] | N.D. |
| all-trans retinol by HPLC (IU) | |
| Fraction I[a] | 395.57 |
| Fraction II[b] | 440.47 |
| cholecalciferol by HPLC (IU) | |
| Fraction I[a] | N.D. |
| Fraction II[b] | N.D. |

Data from Professor Robert Ackman's laboratory, Canadian Institute of Fisheries Technology, Halifax, Nova Scotia.
Data expressed per gram of krill oil.
[a]Extraction made with a sample-acetone ratio of 1:6 (w/v), incubated 2 h at 4° C.
[b]Extraction made with a sample-ethyl acetate ratio of 1:2 (w/v), incubated 30 min at 4° C., following a first extraction with acetone.
TR = trace
N.D. = not detected
Conversion: Vitamin
alpha-tocopherol    mg/g oil × 1.36 = International Unit
All-trans retinol    µg/g ÷ 0.3 = International Unit

TABLE 17

ASTAXANTHIN AND CANTHAXANTHIN CONTENT OF KRILL OIL (*E. pacifica*)

| Asthaxantin (µg/g oil) | |
|---|---|
| Fraction I[a] | 93.1 |
| Fraction II[b] | 121.7 |
| Canthaxanthin (µg/g oil) | |
| Fraction I[a] | 270.4 |
| Fraction II[b] | 733.0 |

Data from Professor Robert Ackman's laboratory, Canadian Institute of Fisheries Technology, Halifax, Nova Scotia.
[a]Extraction made with a sample-acetone ratio of 1:6 (w/v), incubated 2 h at 4 ° C.
[b]Extraction made with a sample-ethyl acetate ratio of 1:2 (w/v), incubated 30 min at 4° C., following a first extraction with acetone.

TABLE 18

OPTIMAL CONDITIONS FOR LIPID EXTRACTION OF AQUATIC ANIMAL TISSUES (suggested procedure)

| STEP | CONDITIONS |
|---|---|
| Grinding (if particles >5 mm) | 4° C. |
| Lipid extraction | sample-acetone ratio of 1:6 (w/v) 2 h (including swirling 20 min) 4° C. |
| Filtration | organic solvent resistant filter under reduced pressure |
| Washing | sample-acetone ratio of 1:2 (w/v) pure and cold acetone |
| Filtration | organic solvent resistant filter under reduced pressure |
| Evaporation | under reduced pressure |
| Oil-water separation | 4° C. |
| Lipid extraction | sample: ethyl acetate ratio of 1:2 (w/v)[a] pure ethyl acetate 30 min 4° C.[b] |
| Filtration | organic solvent resistant filter under reduced pressure |
| Evaporation | under reduced pressure |

[a]Ethanol can be replaced by isopropanol, t-butanol or ethyl acetate.
[b]25° C. when using t-butanol.

TABLE 19

PROTEOLYTIC ACTIVITY OF KRILL RESIDU USING LACTOSERUM AS THE SUBSTRATE, AT 37° C., PH 7.0 FOR A RATIO ENZYME:SUBSTRATE OF 1:43

| Time (min) | Amino acids released (µmoles) | Enzymatic rate (µmoles/min) | Specific enzymatic activity (µmoles/min/mg*) |
|---|---|---|---|
| 15 | 28.76 | 1.917 | 0.164 |
| 30 | 43.74 | 0.999 | 0.125 |
| 170 | 98.51 | 0.322 | 0.050 |
| 255 | 177.26 | 0.308 | 0.060 |

*total quantity of enzymes in hydrolysis media

What is claimed is:

1. A method for extracting total lipid fractions from marine and aquatic animal material, said method comprising the steps of:
   (a) placing marine and aquatic animal material in a ketone solvent to achieve extraction of the soluble lipid fraction from said marine and aquatic animal material;
   (b) separating the liquid and solid contents;
   (c) recovering a first total lipid rich fraction from the liquid contents of b) by evaporation of the solvent present in the liquid contents;
   (d) placing said solid contents in an organic solvent selected from the group of solvents consisting of alcohol and esters of acetic acid to achieve extraction of the remaining soluble total lipid fraction from said marine and aquatic animal material;
   (e) separating the liquid and solid contents;
   (f) recovering a second total lipid rich fraction by evaporation of the solvent from the liquid contents of e); and
   (g) recovering the solid contents.

2. A method as in claim 1, wherein steps (b) and (d) are conducted under inert gas atmosphere.

3. A method as in claim 1, wherein steps (b) and (e) are effected by techniques selected from the group consisting of filtration, centrifugation and sedimentation.

4. A method as in claim 1, wherein steps (c) and (f) are effected by techniques selected from the group consisting of vacuum evaporation, flash evaporation and spray drying.

5. A method as in claim 1, wherein after step (b) and before step (c), the method additionally comprises the intervening step of washing the solid contents with the solvent and adding the resulting washing solution to the liquid contents of step (b).

6. A method as in claim 1, wherein after step (e) and before step (f), the method additionally comprises the intervening step of washing the solid contents with the organic solvent selected in step (d).

7. A method as in claim 1, wherein prior to step (a) the marine and aquatic animal material is finely divided.

8. A method as in claim 1, wherein steps (a) and (b) are conducted at solvent temperatures of not more than about 5° C.

9. A method as in claim 1, wherein said marine and aquatic animal is zooplankton.

10. A method as in claim 9, wherein said zooplankton is selected from krill and Calanus.

11. A method as in claim 1, wherein said marine and aquatic animal is fish.

12. A method for extracting an astaxanthin-and-canthaxantin-containing total lipid fraction from a marine and aquatic animal material selected from zooplankton and fish, said method comprising the steps of:
  (a) placing said animal material in a ketone solvent to achieve an extraction of the soluble lipid fraction from said marine and aquatic animal material;
  (b) separating the liquid and solid contents; and
  (c) recovering a lipid rich fraction from the liquid contents by evaporation of the solvent present in the liquid contents,
  whereby an astaxanthin-and-canthaxantin-containing total lipid fraction is obtained.

13. A method for extracting a total lipid fraction from a marine and aquatic animal material selected from zooplankton and fish, said method comprising the steps of:
  (a) placing said animal material in a solvent mixture comprising acetone and ethanol to achieve an extraction of the soluble lipid fraction from said marine and aquatic animal material;
  (b) separating the liquid and solid contents; and
  (c) recovering a lipid rich fraction from the liquid contents by evaporation of the solvents present in the liquid contents,
  whereby a total lipid fraction is obtained.

14. A method as in claim 12, wherein the animal material is selected from krill and Calanus.

15. A method as in any one of claim 12, wherein during step (a), the animal material is homogenized.

16. A method as in claim 12, wherein steps (b) and (d) are conducted under inert gas atmosphere.

17. A method as in claim 12, wherein step (b) is effected by a technique selected from the group consisting or nitration, centrifugation and sedimentation.

18. A method as in claim 12, wherein step (c) is effected by a technique selected from the group consisting of vacuum evaporation, flash evaporation and spray drying.

19. A method as in claim 12, wherein after step (b) and before step (c), the method additionally comprises a step of washing said solid contents with solvent and adding the resulting washing solution to the liquid contents of step (b).

20. A method as in claim 12, wherein prior to step (a) the marine and aquatic animal material is finely divided.

21. A method as in claim 12, wherein steps (a) and (b) are conducted at solvent temperatures of about 5° C. or less.

22. A method of lipid extraction as in claim 1, wherein the solid contents of step b) is recovered and consists of a dehydrated residue containing active enzymes.

23. A method of lipid extraction as in claim 12, wherein the solid contents of step b) is recovered and consists of a dehydrated residue containing active enzymes.

24. A method for extracting total lipid fractions from marine and aquatic animal material, said method comprising the steps of:
  (a) placing marine and aquatic animal material in a ketone solvent to achieve extraction of the soluble total lipid fraction from said marine and aquatic animal material;
  (b) separating the liquid and solid contents;
  (c) recovering a first total lipid-rich fraction from the liquid contents of b) by evaporation of the solvent present in the liquid contents;
  (d) placing said solid contents in an organic solvent selected from the group of solvents consisting of alcohol and esters of acetic acid to achieve extractions of the remaining soluble total lipid fraction from said marine and aquatic animal material;
  (e) separating the liquid and solid contents; and
  (f) recovering a second total lipid-rich fraction try evaporation of the solvent from the liquid contents of e),
  whereby total lipid fractions are obtained.

25. A method of total lipid extraction as in claim 24, wherein the solid contents of step b) is recovered and consists of a dehydrated residue containing active enzymes.

26. A method as in claim 1, wherein the ketone solvent is acetone.

27. A method as in claim 1, wherein the alcohol is selected from the group consisting of ethanol, isopropanol and t-butanol.

28. A method as in claim 1, wherein the ester of acetic acid is ethyl acetate.

29. A method as in claim 7, wherein the marine and aquatic animal material is finely divided to an average particle size of not more than 5 mm.

30. A method as in claim 12, wherein said marine and aquatic animal material is viscera.

31. A method as in claim 12, wherein the ketone solvent is acetone.

32. A method as in claim 13, wherein said marine and aquatic animal material is viscera.

33. A method as in claim 13, wherein the animal material is selected from krill and Calanus.

34. A method as in claim 20, wherein the animal material is finely divided to an average particle size of not more than 5 mm.

35. A method as in claim 1, wherein the solid contents of step (e) is recovered and consists of a dehydrated residue containing active enzymes.

36. A method as in claim 24, wherein the ketone solvent is acetone.

37. A method as in claim 24, wherein the alcohol is selected from the group of ethanol, isopropanol and t-butanol.

38. A method as in claim 24, wherein the ester of acetic acid is ethyl acetate.

39. A method of lipid extraction as in claim 24, wherein the solid contents of step (3) is recovered and consists of a dehydrated residue containing active enzymes.

* * * * *

UNITED STATES PATENT AND TRADEMARK OFFICE
CERTIFICATE OF CORRECTION

| | | |
|---|---|---|
| PATENT NO. | : 6,800,299 B1 | Page 1 of 2 |
| APPLICATION NO. | : 09/830146 | |
| DATED | : October 5, 2004 | |
| INVENTOR(S) | : Beaudoin et al. | |

It is certified that error appears in the above-identified patent and that said Letters Patent is hereby corrected as shown below:

Title Page #75 INVENTORS, replace "Sherbrooke" with --Quebec--

FOREIGN PATENT DOCUMENTS, Line 8 delete (the second listing of) "JP 04057853 2/1992"

FOREIGN PATENT DOCUMENTS, Line 9 delete "JP 08198754 6/1996"

OTHER PUBLICATIONS, Line 8 insert --Chemical Abstracts no. 177859, vol. 98, no. 21 "Isolation of astaxanthin from crayfish or shrimp waste for use as a coloring agent in fish feed" March 23, 1983.--

OTHER PUBLICATIONS, Col. 2 line 1 replace "Chäteau" with --Château--

OTHER PUBLICATIONS, Col. 2 line 6 replace "Mitake" with --Mitaka--

OTHER PUBLICATIONS, Col. 2 line 11 replace "conbinatorial" with --combinatorial--

OTHER PUBLICATIONS, Col. 2 line 15 replace "Alvarea" with --Alvarez--

OTHER PUBLICATIONS, Col. 2 line 15 replace "Arangea" with --Aranega--

OTHER PUBLICATIONS, Col. 2 line 28 replace "Granzow.." with --Granzow.--

OTHER PUBLICATIONS, Col. 2 line 31 replace "DiPrimo" with --DiPrimio--

OTHER PUBLICATIONS, Col. 2 line 34 replace "Curevo" with --Cuervo--

Column 5, line 40, make new paragraph at "Table 1"

Column 8, line 29, replace "with" with --to--

Column 9, line 15, replace "Heligren" with --Hellgren--

Column 11, line 6, replace "(M. norv gica)" with --(M. norvegica)--

Column 11, line 51, replace "(Macker l) with --(Mackerel)--

Column 12, line 4, replace "(Macker l)" with --(Mackerel)--.

UNITED STATES PATENT AND TRADEMARK OFFICE
CERTIFICATE OF CORRECTION

PATENT NO.        : 6,800,299 B1
APPLICATION NO.   : 09/830146
DATED             : October 5, 2004
INVENTOR(S)       : Beaudoin et al.

It is certified that error appears in the above-identified patent and that said Letters Patent is hereby corrected as shown below:

Column 12, line 55, replace "4°." with --4° C.--

Column 13, line 27, insert --3-- before "chlor:MeOHd"

Column 13, line 44, insert --3-- before "chlor:MeOHd"

Column 13, line 63, "Wijs iodine index" should be underlined

Column 16, line 15, replace "0.1" with --0.2--

Column 16, line 38, replace "16:3 n-3 + I 17:1" with --16:3 n-4 + I 17:1--

Column 17, line 12, replace "Fraction Ib" with --Fraction IIb--

Column 19, line 51, replace "nitration" with --filtration--

Column 20, line 22, replace "try" with --by--

Signed and Sealed this

Ninth Day of January, 2007

JON W. DUDAS
*Director of the United States Patent and Trademark Office*